US006778923B2

United States Patent
Norris et al.

(10) Patent No.: US 6,778,923 B2
(45) Date of Patent: Aug. 17, 2004

(54) REDUCED CROSS TALK PULSE OXIMETER

(75) Inventors: Mark A. Norris, Louisville, CO (US); D. Alan Hanna, Boulder, CO (US)

(73) Assignee: DatexθOhmeda, Inc., Madison, WI (US)

( * ) Notice: Subject to any disclaimer, the term of this patent is extended or adjusted under 35 U.S.C. 154(b) by 48 days.

(21) Appl. No.: 10/147,452

(22) Filed: May 15, 2002

(65) Prior Publication Data

US 2003/0028357 A1 Feb. 6, 2003

Related U.S. Application Data

(63) Continuation-in-part of application No. PCT/US01/43610, filed on Nov. 15, 2001, and a continuation-in-part of application No. 09/712,864, filed on Nov. 15, 2000, now Pat. No. 6,505,133.

(51) Int. Cl.[7] .............................................. G01R 13/00
(52) U.S. Cl. ......................................................... 702/74
(58) Field of Search ................................ 702/74, 76, 79, 702/69; 600/309, 310, 386; 275/316, 346

(56) References Cited

U.S. PATENT DOCUMENTS

| 4,800,885 A | 1/1989 | Johnson ...................... 128/633 |
| 4,819,752 A | 4/1989 | Zelin ........................... 128/633 |
| 4,848,901 A | 7/1989 | Hood, Jr. ...................... 356/41 |
| 4,930,140 A | 5/1990 | Cripps et al. .................. 375/1 |
| 4,972,331 A | 11/1990 | Chance ........................ 364/550 |
| 5,122,974 A | 6/1992 | Chance ........................ 364/550 |
| 5,193,543 A | 3/1993 | Yelderman ................... 128/633 |
| 5,204,874 A | 4/1993 | Falconer et al. ................ 375/1 |
| 5,277,181 A | 1/1994 | Mendelson et al. ......... 128/633 |
| 5,320,098 A | 6/1994 | Davidson ..................... 128/630 |
| 5,343,818 A | 9/1994 | McCarthy et al. ........... 128/633 |
| 5,349,952 A | 9/1994 | McCarthy et al. ........... 128/633 |
| 5,349,953 A | 9/1994 | McCarthy et al. ........... 128/633 |
| 5,387,259 A | 2/1995 | Davidson ..................... 128/630 |
| 5,460,182 A | 10/1995 | Goodman et al. ........... 128/664 |
| 5,766,127 A | 6/1998 | Pologe et al. ................ 600/310 |
| 5,769,791 A | 6/1998 | Benaron et al. ............. 600/473 |
| 5,772,597 A | 6/1998 | Goldberger et al. ......... 600/473 |

(List continued on next page.)

FOREIGN PATENT DOCUMENTS

JP            06-303629        * 10/1994

*Primary Examiner*—Michael Nghiem
(74) *Attorney, Agent, or Firm*—Marsh, Fischmann & Breyfogle LLP

(57) ABSTRACT

A system and method of reducing cross talk in pulse oximetry signals that are attenuated by a patient tissue site are provided. In one embodiment, Red and IR LEDs of a pulse oximeter are separately excited (1010) and the respective Red and IR data vectors output by the detector are measured (1020). The Red and IR data vectors are normalized (1030). Red to IR and IR to Red cross talk vectors are computed (1040). Red and IR demodulation vectors are obtained by subtracting (1050) the respective Red and IR cross talk vectors from the respective normalized Red and IR data vectors. The demodulation vectors are normalized (1060), scaled (1070), and the magnitudes of the Red and IR signal components are obtained by computing (1080) the dot product of the composite signal data vector with the normalized and scaled Red demodulation and IR demodulation vectors, respectively.

27 Claims, 12 Drawing Sheets

U.S. PATENT DOCUMENTS

| | | | | |
|---|---|---|---|---|
| 5,774,213 A | | 6/1998 | Trebino et al. | 356/320 |
| 5,782,758 A | | 7/1998 | Ausec et al. | 600/336 |
| 5,785,658 A | | 7/1998 | Benaron et al. | 600/473 |
| 5,800,348 A | | 9/1998 | Kaestle | 600/322 |
| 5,805,583 A | | 9/1998 | Rakib | 370/342 |
| 5,807,261 A | | 9/1998 | Benaron et al. | 600/473 |
| 5,891,022 A | | 4/1999 | Pologe | 600/323 |
| 5,891,024 A | | 4/1999 | Jarman et al. | 600/323 |
| 5,919,134 A | * | 7/1999 | Diab | 600/323 |
| 5,921,921 A | | 7/1999 | Potratz et al. | 600/323 |
| 5,934,277 A | | 8/1999 | Mortz | 128/633 |
| 5,995,858 A | | 11/1999 | Kinast | 600/323 |
| 6,097,712 A | | 8/2000 | Secord et al. | 370/335 |
| 6,229,856 B1 | | 5/2001 | Diab et al. | 375/316 |
| 6,269,267 B1 | | 7/2001 | Bardy et al. | 607/5 |
| 6,363,269 B1 | * | 3/2002 | Hanna et al. | 600/322 |
| 6,397,092 B1 | * | 5/2002 | Norris et al. | 600/323 |
| 6,505,060 B1 | * | 1/2003 | Norris | 600/323 |
| 6,505,133 B1 | * | 1/2003 | Hanna et al. | 702/74 |
| 6,510,329 B2 | * | 1/2003 | Heckel | 600/310 |
| 2003/0073890 A1 | * | 4/2003 | Hanna | 600/323 |

\* cited by examiner

REDUCED CROSS TALK PULSE OXIMETER

RELATED APPLICATION INFORMATION

The present application claims the benefit under 35 U.S.C. 120 and is a continuation in part of U.S. patent application Ser. No. 09/712,864, now U.S. Pat. No. 6,505,133, entitled "SIMULTANEOUS SIGNAL ATTENUATION MEASUREMENTS UTILIZING CODE DIVISION MULTIPLEXING" filed Nov. 15, 2000, and International Application Serial No. PCT/US01/43610 entitled "SIMULTANEOUS SIGNAL ATTENUATION MEASUREMENTS UTILIZING CODE DIVISION MULTIPLEXING" filed Nov. 15, 2001, and designating the United States, which are hereby incorporated in their entirety herein.

FIELD OF THE INVENTION

The present invention relates in general to simultaneous signal attenuation measurement systems and, in particular, to reducing undesired cross talk in pulse oximeters and other such systems that identify attenuation characteristics associated with individual signal components.

BACKGROUND OF THE INVENTION

Signal attenuation measurements generally involve transmitting a signal towards or through a medium under analysis, detecting the signal transmitted through or reflected by the medium and computing a parameter value for the medium based on attenuation of the signal by the medium. In simultaneous signal attenuation measurement systems, multiple signals are simultaneously transmitted (i.e., two or more signals are transmitted during at least one measurement interval) to the medium and detected in order to obtain information regarding the medium.

Such attenuation measurement systems are used in various applications in various industries. For example, in the medical or health care field, optical (i.e., visible spectrum or other wavelength) signals are utilized to monitor the composition of respiratory and anesthetic gases, and to analyze tissue or a blood sample with regard to oxygen saturation, analyte values (e.g., related to certain hemoglobins) or other composition related values.

The case of pulse oximetry is illustrative. Pulse oximeters determine an oxygen saturation level of a patient's blood, or related analyte values, based on transmission/absorption characteristics of light transmitted through or reflected from the patient's tissue. In particular, pulse oximeters generally include a probe for attaching to a patient's appendage such as a finger, earlobe or nasal septum. The probe is used to transmit pulsed optical signals of at least two wavelengths, typically red and infrared, to the patient's appendage. The transmitted signals are received by a detector that provides an analog electrical output signal representative of the received optical signals. By processing the electrical signal and analyzing signal values for each of the wavelengths at different portions of a patient pulse cycle, information can be obtained regarding blood oxygen saturation.

Such pulse oximeters generally include multiple sources (emitters) and one or more detectors. A modulation mechanism is generally used to allow the contribution of each source to the detector output to be determined. Conventional pulse oximeters generally employ time division multiplexing (TDM) signals. As noted above, the processing of the electrical signals involves separate consideration of the portions of the signal attributable to each of the sources. Such processing generally also involves consideration of a dark current present when neither source is in an "on" state. In TDM oximeters, the sources are pulsed at different times separated by dark periods. Because the first source "on" period, the second source "on" period and dark periods occur at separate times, the associated signal portions can be easily distinguished for processing.

Alternatively, pulse oximeters may employ frequency division multiplexing (FDM) signals. In the case of FDM, each of the sources is pulsed at a different frequency resulting in detector signals that have multiple periodic components. Conventional signal processing components and techniques can be utilized to extract information about the different frequency components.

In order to accurately determine information regarding the subject, it is desirable to minimize noise in the detector signal. Such noise may arise from a variety of sources. For example, one source of noise relates to ambient light incident on the detector. Another source of noise is electronic noise generated by various oximeter components. Many significant sources of noise have a periodic component.

Various attempts to minimize the effects of such noise have been implemented in hardware or software. For example, various filtering techniques have been employed to filter from the detector signal frequency or wavelength components that are not of interest. However, because of the periodic nature of many sources of noise and the broad spectral effects of associated harmonics, the effectiveness of such filtering techniques is limited. In this regard, it is noted that both TDM signals and FDM signals are periodic in nature. Accordingly, it may be difficult for a filter to discriminate between signal components and noise components having a similar period.

Cross talk may also be a significant source of undesirable noise in pulse oximeters. As previously mentioned, pulse oximeters measure the attenuation of various color light signals such as, for example, Red and Infra-Red (IR) wavelength signals that are transmitted through or reflected from a suitable patient tissue site. The different colors of light employed by the pulse oximeter may be referred to as channels (e.g., the Red channel and the IR channel). The attenuation measurements for each channel include a time varying component due to pulsing of the patient's arterial blood and a static component due to absorption of the light signals by venous blood, tissues and other bodily structures. By employing a ratio of the time varying component of the measured attenuation normalized by the static component of the measured attenuation for each channel, pulse oximeters are insensitive to the absolute signal strength of each color light signal and amplitude measurements of each color light signal transmitted through or reflected from the tissue site can be used to compute the patient's oxygen saturation (SpO2) level. However, offsets, feed throughs and other cross talks that add signal to any of the measured amplitudes can result in errors in the normalized attenuations, thus resulting in errors in the SpO2 level computed therefrom. For example, system bandwidth limitations and photodetector tailing smear the signal from the emitter. In this regard, the pulse oximeter system may detect the emitter for a particular color light signal as being on when it is off. This smearing feeds the signal from one emitter into the signal(s) from the other emitter(s) resulting in undesired cross talk from one channel into the other channel(s) of the oximeter. By way of further example, some portion of the emitter drive signal(s) may be capacitively coupled into the detector. Such capacitive cross talk creates an offset in the pulse oximeter system that varies between particular probe cable/detector units.

SUMMARY OF THE INVENTION

The present invention is directed to a simultaneous signal attenuation measurement system employing code division multiplexing (CDM). The invention allows for analysis of a multiplexed signal to distinguish between two or more signal components thereof based on codes modulated into the signal components. The CDM codes are nonperiodic thereby facilitating various processing techniques for distinguishing the signals of interest from noise or other interference. Moreover, the invention allows for a variety of hardware and processing options that may reduce costs, simplify system operation and improve accuracy of the attenuation measurements. Further, a reduced cross talk pulse oximetry system and method are provided by the present invention. The reduced cross talk pulse oximetry system and method achieve improved accuracy of pulse oximetry measurements using code division multiplexed modulated drive signal waveforms by utilizing demodulation waveforms that are optimized relative to the attenuated light signal components as output by the detector rather than the modulated drive signal waveforms.

According to one aspect of the present invention, codes are modulated into the transmitted signals of a signal attenuation measurement system. The system includes at least two signal sources (e.g., having different wavelengths) that are pulsed by source drives to a medium under analysis. One or more detectors receive the first and second signal from the medium (e.g., after transmission through or reflection from the medium) and output a composite signal reflecting contributions corresponding to each of the transmitted source signals. The detector signal is thus a multiplexed signal composed of at least two signal components. In accordance with the present invention, the source drives are operated to modulate each of the source signals based on a nonperiodic signal or a code. For example, each drive may pulse a corresponding one of the signal sources between a high output or "on" state and a low value or "off" state. It will be appreciated that, depending on the sources employed, substantial photonic energy may be transmitted in the nominal "off" state. Accordingly, in the context of the source signals, a code may be conceptualized as a bit stream of "0s" and "1s", where "0" corresponds to an off state, "1" corresponds to an on state, and the bit length corresponds to a base unit of time that generally reflects the shortest pulse length utilized in driving the sources.

The codes define source signals that have nonperiodic characteristics. That is, due to the codes, there is at least a component of each source signal that is not described by a regularly repeating temporal pattern. As will be understood from the description below, however, the codes themselves may be concatenated in the source signal and a periodic modulating signal may carry the coded signal.

A number of preferred characteristics have been identified for the codes. Among these are:
1. the codes for the different sources are preferably mathematically orthogonal;
2. the numbers of 1s and 0s in a code should be about the same;
3. the distribution of 1s and 0s within a code should be fairly even; and
4. the distribution of transitions between 1s and 0s within a code should be fairly even.

These preferences and some bases therefor are described in detail below. The codes utilized in accordance with the present invention preferably have one or more of these characteristics and, more preferably, have all of the noted characteristics.

According to another aspect of the invention, a detector signal is processed in a signal attenuation measurement system to demultiplex the detector signal and extract component information therefrom based on nonperiodic codes. In particular, the detector signal is first processed to provide a processed signal for demultiplexing and the processed signal is then demultiplexed using at least one coded demultiplexing signal that includes a series of values defining a nonperiodic code. Information is thereby obtained regarding first and second signal components of the detector signal. This information can be utilized in an attenuation analysis to determine an attenuation related parameter of a medium under analysis.

The initial processing of the detector signal may include various processing steps and components depending on the specific application and implementation. For example, where the detector signal is an analog signal, initial processing may involve analog to digital conversion. Preferably, such conversion is implemented using a fast analog to digital converter that digitally samples the detector signal multiple times per source cycle. Such a converter in combination with processing techniques enabled by code division multiplexing allows for improved measurement accuracy and hardware implementation options for certain attenuation measurement applications. The initial processing may further or alternatively include signal filtering to reduce undesired components, signal amplification including, e.g., DC rectification to remove or avoid amplifying DC or low frequency components especially in the case of DC coupled sources, and/or other signal enhancement processing.

Preferably, the demultiplexing process involves the use of a unique demultiplexing signal for each signal component of interest, e.g., corresponding to each signal source. In this regard, the same codes used for modulating the source signals may be used to demodulate the detector signal. However, for mathematical convenience, the demodulating codes may be conceptualized as a series of –1s and +1s rather than 0s and 1s as discussed above in relation to the modulating codes. The coded demodulating signal may be filtered to compensate for certain wave shape distortions resulting from bandwidth limitations and non-linearities and/or to reduce response at certain frequencies. In addition, the codes may be pre-computed to reduce processing requirements.

It has been found that simply establishing orthogonality of the demodulation functions or vectors based on the modulating signals of the source drives can result in some degree of cross-talk between the channels or impaired noise rejection. In particular, due to distortions resulting from transmission and processing of the signal between the code generator and the digital processing unit that receives the digitized detector signal, as well as other sources of noise, the received signal may vary relative to the transmitted code. Improved performance can be achieved by establishing the demodulation vectors relative to the received signals rather than the originally generated codes.

Moreover, optimization of the demodulation vectors in this regard can be implemented for specific operating environments such as hardware configurations. That is, code distortion may depend on the specific hardware components employed including, in the case of pulse oximetry, the sources, source drive circuitry, cables, detector, detector output circuitry, the components used for amplification and other signal conditioning, the A/D converter and associated circuitry, as well as non-equipment factors such as the transmission medium and effective optical pathlength (including whether the oximetry probe is attached to a finger, ear lobe, nasal septum, etc.) and other ambient influences. For many pulse oximetry applications, the principal variable in this regard is the identity of the probe that is attached to the patient's appendage.

The use of an oversampling A/D converter as discussed above allows for substantial processing resolution in "matching" the demodulation vector to the received code. In particular, an oversampling converter may provide many samples per modulation signal pulse cycle, e.g., 20 or more samples, thereby enabling accurate definition of the demodulation vectors for a particular operating environment.

Thus, in accordance with another aspect of the present invention, a demodulation unit for use in a modulated signal system is provided. The modulated signal system includes: a modulation signal generator for generating at least first and second modulation signals; signal transmitting and processing components for transmitting a signal of interest based on the modulation signals and processing the transmitted signal; and a processor for receiving the resulting processed signal. The demodulation vector unit is operative for providing demodulation vectors for use by the processor in demodulating at least two components of the processed signal, where the demodulation vectors are based on the expected processed signal and reflect demodulation signals that are different than the modulation signals.

In a preferred implementation, the modulating signals reflect at least two mutually orthogonal codes for modulating at least two components of the transmitted signal and the demodulating vectors are defined to be orthogonal with respect to each of the components as received at the processor. The modulated signal system may be a pulse oximeter. An associated method involves receiving a processed modulated signal including at least two components modulated in accordance with input modulation signals and demodulating the processed signal using demodulation vectors based on the expected processed signal, where the demodulation vectors reflect demodulation signals that are different than the input modulating signals.

In accordance with another aspect of the present invention, a process is provided for establishing demodulation vectors for a modulated signal system. The system includes a signal generator for transmitting a signal including first and second components modulated in accordance with first and second modulating codes, signal processing components for processing the transmitted signal and a processor for receiving the resulting processed signal. The process for establishing demodulation vectors involves: operating the system to transmit a first transmitted signal corresponding to the first signal component; receiving a first processed signal corresponding to said first transmitted signal as received at the processor; decoding the first transmitted signal to obtain a first received code; generating a first demodulation vector based on (e.g., orthogonal to) the first received code, and repeating such processing steps with regard to a second transmitted signal corresponding to the second signal component.

In the context of pulse oximetry, this process may be conducted as part of a manufacturing or calibration process. For example, demodulation vectors may be established or updated for a given unit, unit type or model based on a variety of operating environments. Thus, a unit under consideration may be operated, for example, in a variety of equipment configurations involving different probes, different cables and/or other equipment variations. For each such permutation of equipment configuration or associated parameters, appropriate demodulation vectors may be established and stored. During use, the appropriate vectors are applied based on the current equipment configuration or operating parameters/conditions.

In accordance with another aspect of the present invention, a demodulation unit is operated based on a recognized operating environment. The demodulation unit is used in connection with a modulated signal system as described above. The system is operated to transmit a signal including at least one component modulated based on a modulation code. The demodulation unit obtains operating environment information related to the processed signal as received at the processor, performs a comparison to stored demodulation information based on the operating environment information, and selectively provides at least one demodulation vector based on the comparison.

The operating environment may be identified manually or automatically. In this regard, a user can manually identify the operating environment by entering appropriate information into the system, for example, in the context of pulse oximetry, identifying the probe, cable and other equipment and/or the patient appendage under consideration. Alternatively, the operating environment may be identified automatically, for example, in the case of pulse oximetry by operating one or more channels of the oximeter to transmit a signal modulated in accordance with known code or codes, and comparing the received signal to a library of processed modulated signals or demodulation vectors to identify any match. In either case, the identified operating environment may be used to select appropriate demodulation vectors or to lock-out unauthorized or otherwise unsupported equipment configurations, thereby better assuring proper performance and patient safety.

According to one more aspect of the present invention, a method for demodulating first and second attenuated signal components within a composite signal output by at least one detector of a pulse oximeter includes the steps of generating first and second demodulation vectors. In this regard, the first and second attenuated signal components correspond to first and second multiplexed signals (e.g., code division multiplexed signals) that are emitted by first and second optical signal sources of the pulse oximeter, attenuated by a patient tissue site and received by the detector. The first demodulation vector generated is for use in demodulating the first attenuated signal component from the composite signal. In this regard, the first demodulation vector is generated to be substantially orthogonal to the second attenuated signal component of the composite signal output by the detector, rather than orthogonal to second signal as emitted from the second optical signal source. The second demodulation vector generated is for demodulating the second attenuated signal component from the composite signal. In this regard, the second demodulation vector is generated to be substantially orthogonal to the first attenuated signal component of the composite signal, rather than orthogonal to the first signal as emitted from the first optical signal source. The method further comprises the steps of demodulating the composite signal with the first and second demodulation vectors to obtain the magnitude of the first and second attenuated signal components, respectively.

In one embodiment, the first and second demodulation vectors are generated prior to using the pulse oximeter, and the first and second demodulation vectors remain fixed while the pulse oximeter is used to monitor a patient. In another embodiment, the first and second demodulation vectors are initially generated prior to using the pulse oximeter to monitor a patient, and the first and second demodulation vectors are then adjusted dynamically while the pulse oximeter is used. In this regard, the first and second demodulation vectors may be adjusted by applying one or more correction factors that are dynamically computed from information included in at least the first and second attenuated signal components of the composite signal. For example, where the first and second signals are Red and IR signals and, thus, the first and second signal components are Red and IR signal components, the correction factor(s) applied may, for example, be a Red signal to IR signal component cross talk correction factor, an IR signal to Red signal component cross talk correction factor, a Red optical signal source capacitive coupling to Red signal component correction factor, a Red optical signal source capacitive coupling to IR signal component correction factor, an IR optical signal source capacitive coupling to IR signal component correction factor, and/or an IR optic al signal source capacitive coupling to Red signal component correction factor.

The first and second demodulation vectors may, for example, be generated in the following manner. Only the first optical signal source of the pulse oximeter is operated and a first data vector output from the detector when operating only the first optical signal source is recorded. Likewise, only the second optical signal source of the pulse oximeter is operated, and a second data vector output from the detector when operating only the second optical signal source is recorded. In this regard, each source may be operated through multiple cycles of its modulation drive code and the results averaged to obtain the first and second data vectors. A first scalar value corresponding to cross talk from operation of the second optical signal source into the first data vector is computed and a second scalar value corresponding to cross talk from operation of the first optical signal source into the second data vector is computed. The first and second scalar values may be computed by normalizing the first and second data vectors and computing the dot product of the first and second data vectors. A first correction vector having a direction opposite the direction of the first data vector and a magnitude given by the first scalar value is formed, and a second correction vector having a direction opposite the direction of the second data vector and a magnitude given by the second scalar value is also formed. The first demodulation vector is then obtained by subtracting the first correction vector from the first data vector, and the second demodulation vector is then obtained by subtracting the second correction vector from the second data vector.

According to one more aspect of the present invention, a method of correcting for undesired non-orthogonal signal components and interferences in a composite signal output by a detector of multi-channel pulse oximeter includes the step of demodulating the composite signal using matched filters that correspond, respectively, to first and second signal components present in the composite signal to obtain at least first and second uncorrected demodulated signal components corresponding to the first and second signal components. The method also includes the step of demodulating the composite signal using matched filters corresponding, respectively, to first and second interferences present in the composite signal to obtain at least first and second demodulated interferences. In one embodiment, the first signal component is associated with a Red wavelength light signal that has been attenuated by a patient tissue site, the second signal component is associated with an IR wavelength light signal that has been attenuated by the patient tissue site, the first interference comprises capacitive coupling from a Red wavelength optical signal source into the first signal component, and the second interference comprises capacitive coupling from the IR wavelength optical signal source into the first signal component. Having demodulated the composite signal to obtain the demodulated interferences and uncorrected demodulated signal components, a first corrected demodulated signal component corresponding to the first signal component is then obtained by subtracting the second uncorrected demodulated signal component and the first and second demodulated interferences from the first uncorrected demodulated signal component. The method may further include the step of demodulating the composite signal using matched filters corresponding, respectively, to third and fourth interferences present in the composite signal to obtain at least third and fourth demodulated interferences. In one embodiment, the third interference comprises capacitive coupling from a Red wavelength optical signal source into the second signal component, and the fourth interference comprises capacitive coupling from the IR wavelength optical signal source into the second signal component. Having also demodulated the third and fourth interferences, a second corrected demodulated signal component corresponding to the second signal component is then obtained by subtracting the first uncorrected demodulated signal component and the third and fourth demodulated interferences from the second uncorrected demodulated signal component.

According to one more aspect of the present invention, a reduced cross talk pulse oximetry system includes at least first and second optical signal sources, at least one detector, an analog-to-digital converter, and a digital processor. The first and second optical signal sources are operable to transmit first and second optical signals in response to modulated drive signals (e.g., code division multiplexed drive signals). The detector is operable to detect the first and second signals after the first and second signals are attenuated by a patient tissue site. The detector outputs an analog composite signal including at least first and second attenuated signal components corresponding to the attenuated first and second signals. The analog-to-digital converter is operable to convert the analog composite signal output by the detector to a digital composite signal having a plurality of sample instances. The digital processor is operable to demodulate the digital composite signal with a first demodulation vector to obtain a magnitude of the first attenuated signal component and is also operable to demodulate the digital composite signal with a second demodulation vector to obtain a magnitude of the second attenuated signal component. The first and second demodulation vectors are established relative to the first and second signal components in the composite signal rather than the modulation drive codes used to drive the optical signal sources. In this regard, the first demodulation vector is substantially orthogonal to the second attenuated signal component and the second demodulation vector is substantially orthogonal to the first attenuated signal component.

The reduced cross talk pulse oximetry system may further include a demodulation vector unit that is operable to provide the first and second demodulation vectors to the digital processor. In this regard, the demodulation vector unit may select the first and second demodulation vectors based on identification of an operating environment. For example, the demodulation vector unit may be configured to receive manually entered information from a user of the pulse oximetry system, with the manually entered information identifying the operating environment. The demodulation vector unit may also be configured to automatically identify the operating environment by operating at least one of the optical signal sources to transmit a signal modulated in accordance with a known code and comparing an attenuated signal received by the detector with a library of processed modulated signals.

Once selected by the demodulation vector unit, the first and second demodulation vectors may be fixed during demodulation of the composite signal, or the digital processor may further be operable to dynamically adjust the first and second demodulation vectors provided by the demodulation vector unit during operation of the pulse oximetry system. In this regard, the digital processor may dynamically adjust the first and second demodulation vectors by subtracting one or more correction factors from the first and second demodulation vectors. The digital processor may compute the correction factor(s) for each sample instance of the digital composite signal and adjust the demodulation vectors accordingly. In one embodiment, the first and second optical signal sources are Red and IR LEDs, the first and second signals are Red and IR signals, the first and second signal components are Red and IR signal components, and the correction factor(s) is/are a Red signal to IR signal component cross talk correction factor, an IR signal to Red signal component cross talk correction factor, a Red optical signal source capacitive coupling to Red signal component correction factor, a Red optical signal source capacitive coupling to IR signal component correction factor, an IR optical signal source capacitive coupling to IR signal component correction factor, and/or an IR optical signal source capacitive coupling to Red signal component correction factor.

These and other aspects and advantages of the present invention will be apparent upon review of the following Detailed Description when taken in conjunction with the accompanying figures.

DESCRIPTION OF THE DRAWINGS

For a more complete understanding of the present invention and further advantages thereof, reference is now made to the following detailed description, taken in conjunction with the drawings, in which.

DETAILED DESCRIPTION

The code division multiplexing system of the present invention may be used in a variety of signal attenuation measurement devices. In the following description, the invention is set forth in the context of a pulse oximeter used to measure blood oxygen saturation or related blood analyte values. As will be described below, the invention has particular advantages in the context of pulse oximetry including allowing for improved noise reduction and oximeter component options. However, while pulse oximetry represents a particularly advantageous application of the present invention, it will be understood that various aspects of the present invention are more broadly applicable in a variety of simultaneous signal attenuation measurement contexts.

In the following description, the pulse oximetry environment is first described with reference to a specific pulse oximeter embodiment. Thereafter, specific implementations of the code division multiplexing system of the present invention are described.

Figure 1:
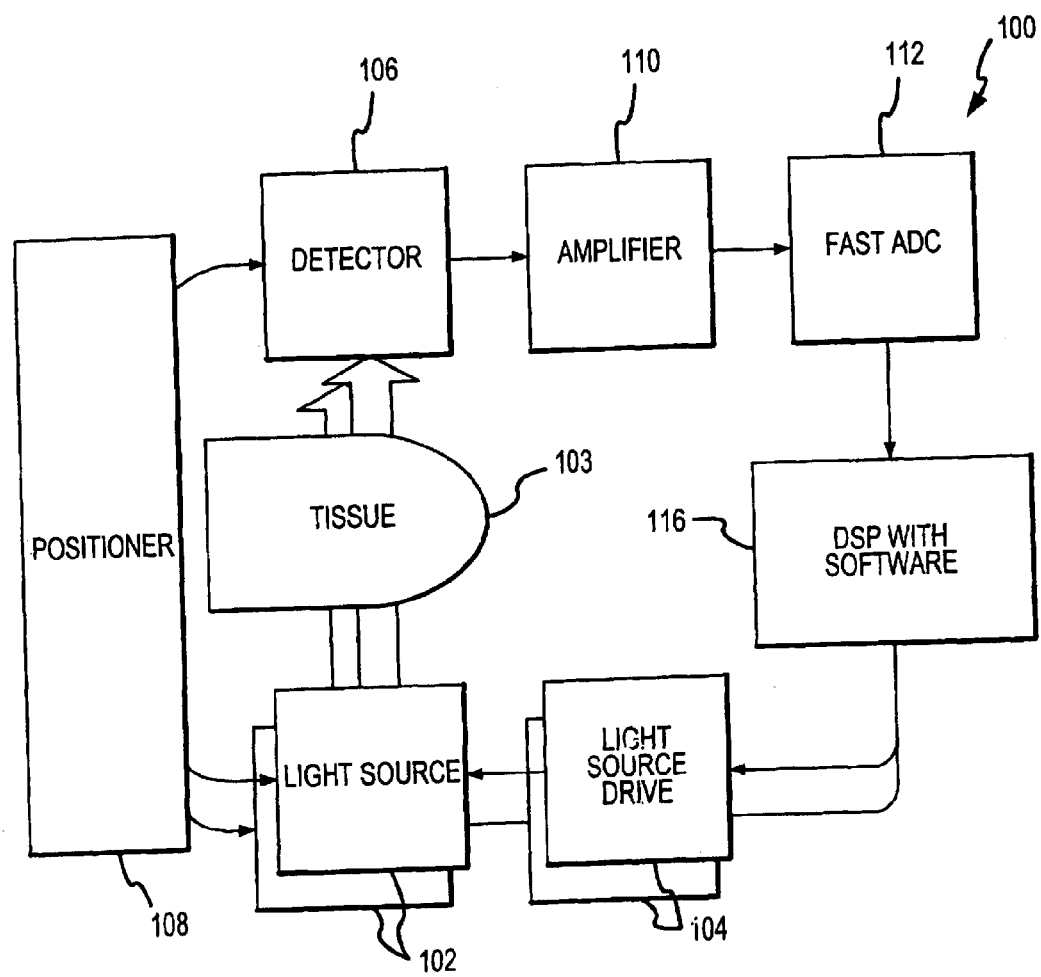
FIG. 1 is a schematic diagram of a pulse oximeter in connection with which the present invention may be implemented.

Referring to FIG. 1, a pulse oximeter in accordance with the present invention is generally identified by the reference numeral 100. The pulse oximeter 100 includes two or more light sources 102 for transmitting optical signals through an appendage 103 of a patient. In the illustrated embodiment, two light sources 102 are shown. For example, the light sources 102 may include a red LED and an infrared LED. The light sources 102 are driven by light source drives 104 in response to drive signals from a digital signal processing unit 116. In the illustrated embodiment, as will be described in more detail below, the signals from the light sources 102 are modulated using different code sequences. For example, the source drive 104 associated with the red light source 102 may pulse the red light source in accordance with a first code sequence and the light source drive 104 associated with the infrared light source 102 may pulse the infrared light source 102 in accordance with a second code sequence different from the first code sequence. It will be appreciated that such a multiplexing system does not result in a periodic signals such as in the case of time division multiplexed or frequency division multiplexed signals. In particular, the pulsing of the sources 102 between "on" and "off" states does not define a regularly repeating waveform. It should also be noted that although the following description references "on" and "off" cycles for each of the sources 102, in reality, the optical signals associated with each source 102 do not define an ideal square wave. For example, substantial photonic energy is emitted even in the "off" state in the case of DC coupled sources. In addition, the intensity transmitted by each of the sources 102 can vary substantially within an "on" cycle. The ability to recognize and address such non-ideal characteristics is an advantage of the present invention.

The optical signals transmitted by the light sources 102 are transmitted through the patient's appendage 103 and impinge upon a detector 106. In this regard, a positioner 108 provides for proper alignment of the sources 102 and the detector 106. Various different types of positioners 108 are available depending, for example, on the appendage to be irradiated and on the patient (e.g. different positioners 108 may be provided for neonatal and adult patients). One typical type of positioner 108 is provided in the form of a clothespin-like clamp which engages a patient's fingertip. When the positioner 108 is engaged on the patient's fingertip, the light sources are positioned on one side of the patient's finger and the detector 106 is positioned on the opposite side in alignment with the light sources so as to receive the optical signals transmitted through the patient's finger. It will be appreciated that, in alternative implementations, a reflective pulse oximeter may be employed whereby the sources and detector are located on the same side of the patient's appendage so as to receive optical signals reflected back from the patient's tissue.

The detector 106 receives the optical signals transmitted through the patient's appendage 103 and provides an analog signal representative of the received optical signals. In the illustrated embodiment, the detector 106 outputs an analog current signal where the magnitude of the current at any given time is proportional to the cumulative intensity of the received optical signals. The detector signal in the illustrated embodiment is then processed by an amplifier circuit 110. The amplifier circuit may serve a number of functions. First, the illustrated amplifier circuit is operative for converting the input analog current signal from the detector 106 into an analog voltage signal. The amplifier circuit 110 may also be operative for subtracting certain DC and low frequency components from the detector signal. For example, one DC component which may be subtracted from the detector signal relates to photonic energy transmitted by the sources 102 during "dark periods." That is, as noted above, practical source implementations generally transmit a signal of some intensity even during off periods. In addition, low frequency ambient light may be subtracted from the detector signal. The amplifier circuit 110 may also filter out certain high frequency electronic noise and provide other signal processing functionality.

The amplifier circuit 110 outputs an analog voltage signal which is representative of the optical signals (or frequency division multiplexed signal) from the sources 102. This analog voltage signal is received by a fast A/D converter 112 which samples the analog voltage signal to generate a digital voltage signal which can be processed by the digital signal processing unit 116. In particular, the converter 112 preferably takes multiple digital samples per cycle of each of the sources 102. That is, the sampling rate of the converter 112 is sufficiently fast to take multiple samples, for example, at least about 20 samples per "on" period of each of the sources 102. Such multiple sampling per cycle allows the oximeter to track the shape of the detector signal, to allow for reduced noise processing of the resulting digital signal and to identify phase components of interest within a signal cycle. Multiple samples per dark period are also obtained. It will thus be appreciated that the values output by the converter 112 are not integrated or aggregate values corresponding to a source cycle period or dark period, but rather, are substantially instantaneous values reflecting the detector signal at a moment within a cycle.

The digital signal processor 116 implements a number of functions. Of particular importance to the present invention, and as will be described in more detail below, the processor 116 includes a demultiplexer module, i.e., the processor executes a variety of demultiplexing software/logic functions including generating or otherwise obtaining a coded demultiplexing signal corresponding to each signal component associated with each source, processing the composite signal using each of the demultiplexing signals to obtain a set of values reflecting the contribution of each source, and using these value sets to obtain instantaneous intensity related values for each of the sources. The processor 116 also includes a parameter calculation module for calculating blood oxygen saturation or related parameter values using known algorithms.

Figure 2:
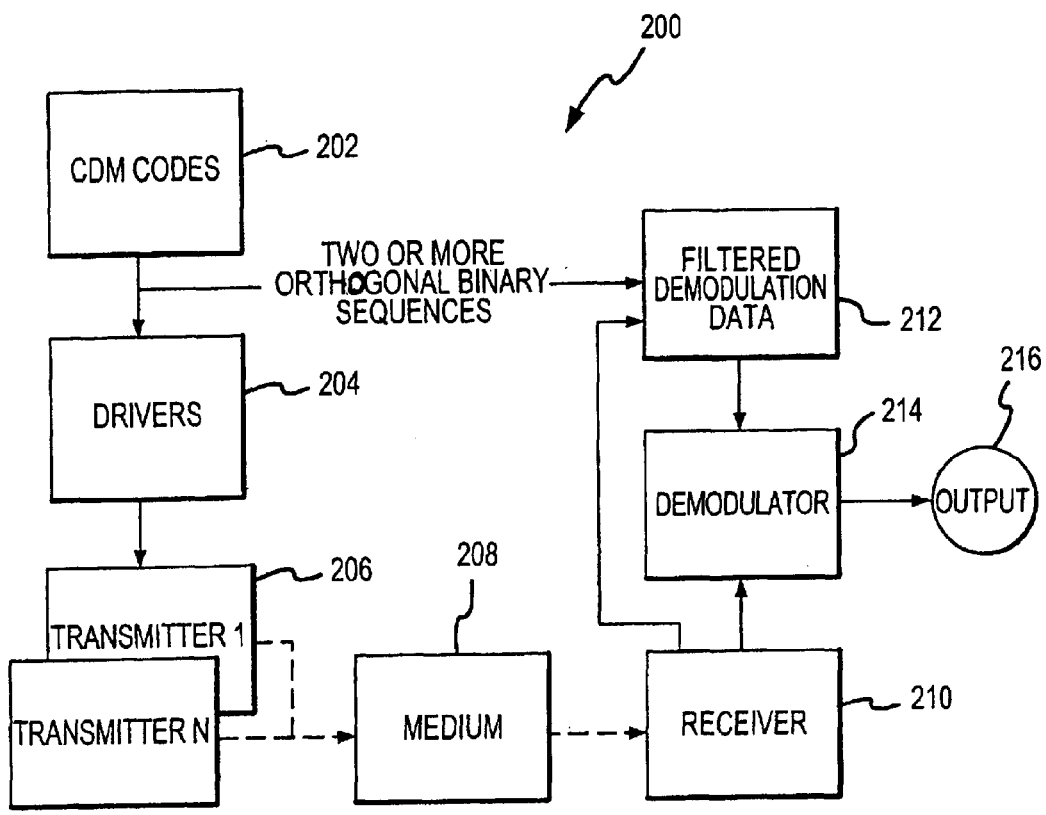
FIG. 2 is a block diagram illustrating a code division multiplexing system in accordance with the present invention.

FIG. 2 illustrates a code division multiplexing system 200 that can be implemented in the pulse oximeter 100 of FIG. 1 in accordance with the present invention. The system 200 includes a code module 202 for providing codes that are used to modulate the sources and demultiplex the detector signal. A number of preferred criteria have been identified with respect to the codes employed. First, these codes are preferably selected, relative to one another, in a manner that allows for processing so as to accurately distinguish the contributions of each of the sources. In this regard, the codes may be substantially orthogonal to reduce any interference between the two signal components, or "channels", corresponding to the two different sources and their wavelengths/spectral composition. As noted above, the codes may be conceptualized as binary sequences. In the context of the sources it is convenient to conceptualize the code sequence in terms of 0 and 1 bits corresponding to the off or low output state, on the one hand, and the on or high output state on the other. In the case of the demultiplexing signal, the bits are conceptualized as −1 and +1 for mathematical convenience. In the following discussion, the −1 and +1 convention is used. The following sequences illustrate the concept of code orthogonality as well as the mathematical convenience of +1s and −1s for a particular processing technique:

$$\begin{array}{rrrr} -1 & 1 & 1 & -1 \\ -1 & -1 & 1 & 1 \\ \hline 1 & -1 & 1 & -1 \end{array}$$

The first line above is a first code sequence and the second line above is a second code sequence. These two code sequences are orthogonal in that half the time that the bit value of the first code is −1, the bit value of the second code is −1 and vice versa. The other half of the time the bit values are opposite. A similar relationship holds for bit values of 1. The third line above is the bit-by-bit product of the first two code sequences. Because the corresponding bits of the codes are the same half of the time (producing a product of +1) and different the other half of the time (producing a product of −1), the sum of the bits in the third line above is 0. By contrast, the sum of the products of two identical codes would be equal to the number of bits in the code. As will be described below, this property facilitates isolation of the portion of the multiplexed detector signal attributable to each of the sources and obtainment of a value indicative of the intensity of that received signal at a given time or time period.

For example, the use of the following eight code segments in equal numbers will allow for generation of a number of suitable orthogonal code sequences:

```
-1       -1  -1  -1
-1       -1   1   1
-1        1  -1   1
-1        1   1  -1
 1       -1  -1   1
 1       -1   1  -1
 1        1  -1  -1
 1        1   1   1
```

It will be observed that these four bit segments include even numbers of −1s and/or +1s allowing for generation of codes based on combinations of these segments that are orthogonal as discussed above. Similar segments of different bit lengths may be used as a basis for generating orthogonal code sequences.

In addition to orthogonality, preferred codes for the illustrated implementation of the invention have a substantially equal number of +1s and −1s. In this manner, introduction of a DC offset is avoided as the code value integrates to zero over relevant intervals.

A further preferred code criterion is that the distribution of +1s and −1s in a code sequence should be relatively even. Most preferably, the numbers of +1s and −1s should be the same in each half of the pattern, each quarter of the pattern, each eighth of the pattern, etc., as far as practicable. Such spreading out of the +1s and −1s in a code sequence reduces the likelihood that low frequency noise will interfere with measured values.

Additionally, it is preferred that the transitions from −1 to +1 and vice versa be substantially evenly distributed in a code sequence so as to provide signals having similar energies. In this regard, it is preferable that the code can be divided into an integer number of segments where the number of transitions in each segment is substantially the same.

The codes can be generated according to the output of a random number generator, by an explicit algorithm, or by a stored series of values. In the case of a random number generator or explicit algorithm process, one or more of the criteria above can be applied by logic running on the digital signal processing platform at run-time. With stored values, the criteria can be applied at run-time or at the time the codes are generated. As discussed below, in one preferred implementation, the codes are pre-generated and stored to reduce processing/storage resource requirements. The codes can then be concatenated in generation of the drive signals.

Figure 3:
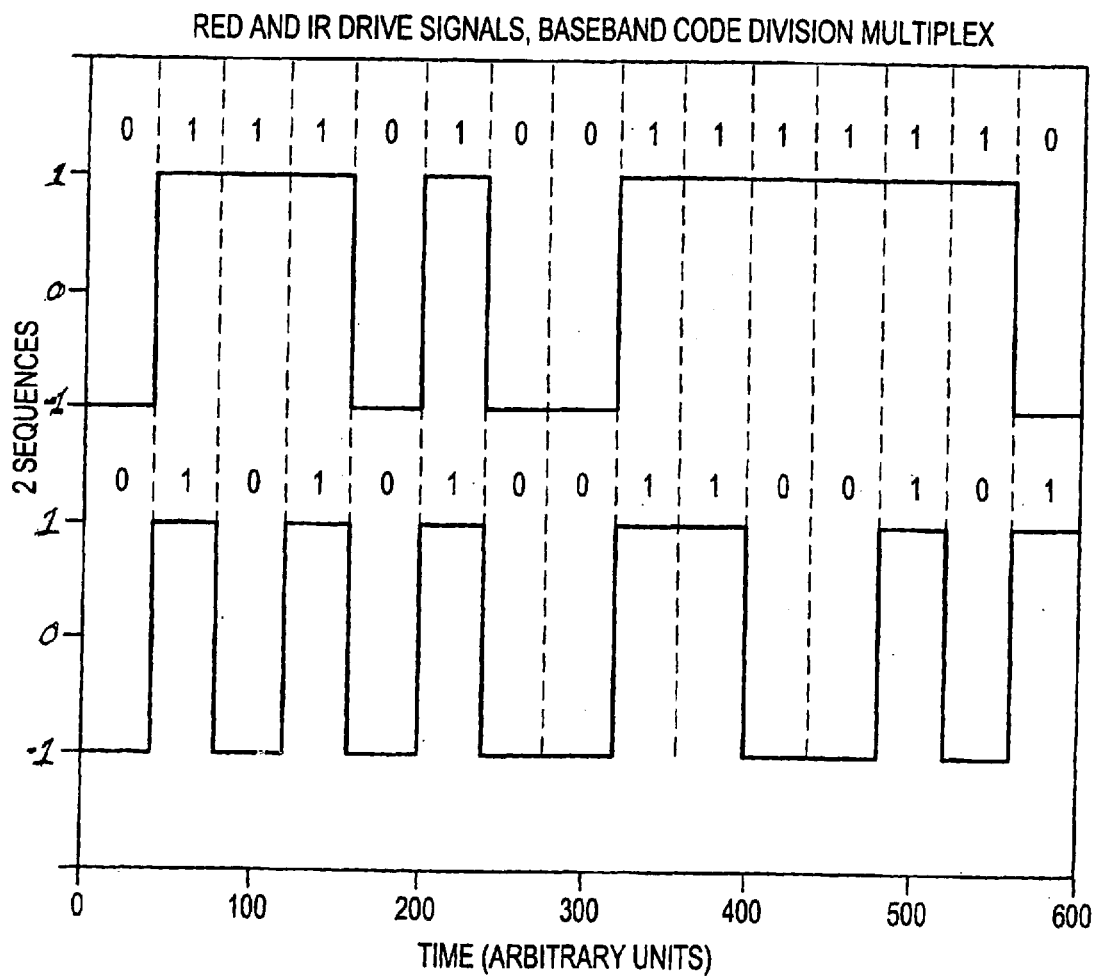
FIG. 3 illustrates two drive signals reflecting codes that may be used in the code division multiplexing system of the present invention.
Figure 4:
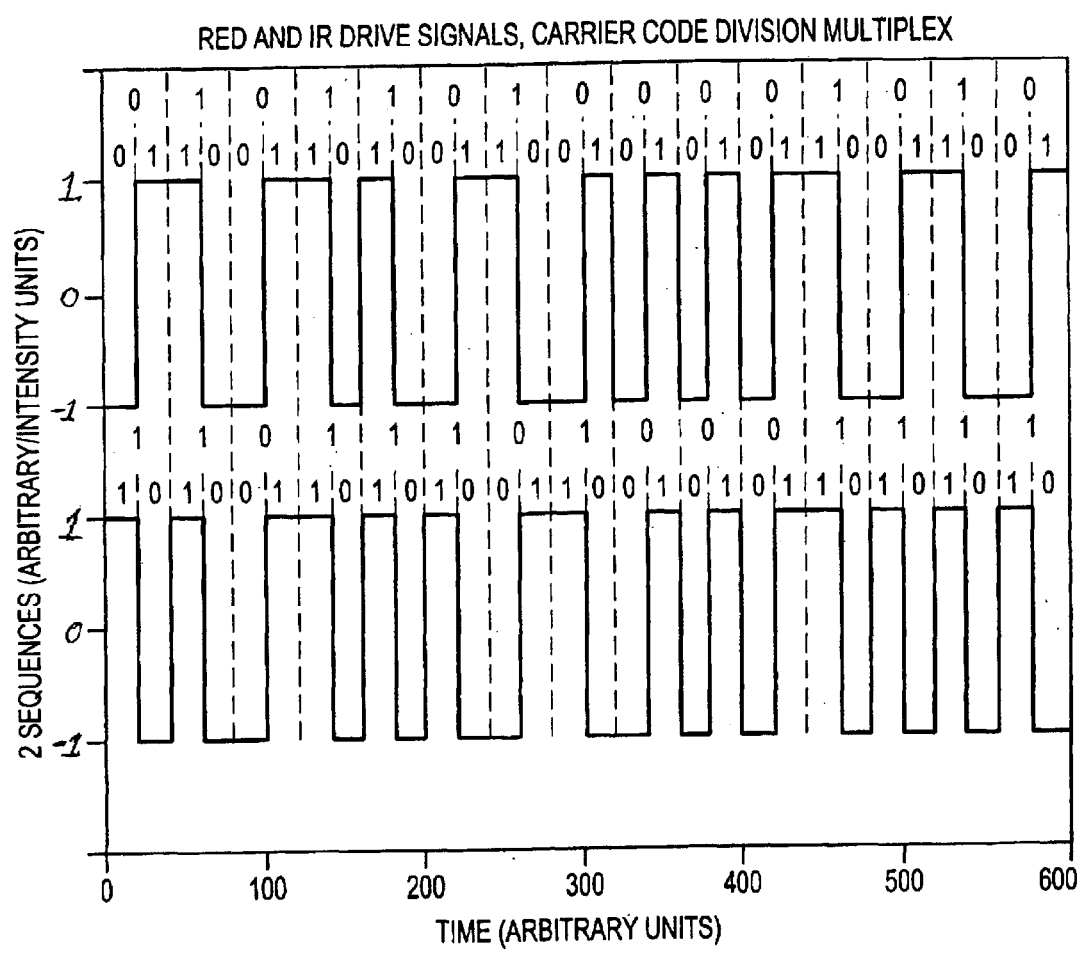
FIG. 4 illustrates two drive signals, reflecting codes transmitted using a carrier wave in accordance with the present invention.

These CDM codes are used by the drivers 204 for the respective sources 206 to encode or modulate the signals transmitted by the sources 206. Such encoded signals are generally illustrated in FIGS. 3–4. For purposes of illustration, FIGS. 3–4 show idealized square waves. It will be appreciated, however, that practical implementations may include waveforms that are somewhat distorted.

FIG. 3 illustrates two code sequences that may be transmitted by two respective sources during a given time period. It will be observed that the illustrated sources are pulsed between an on or high state (+1) and an off or low state (−1). The shortest time period of these states is taken to be a bit length. The resulting code sequences are reproduced above the signal waveforms in FIG. 3. The signals are labeled red and infrared corresponding to two channels commonly used in pulse oximetry. Additional channels or alternative channels may be utilized in accordance with the present invention.

FIG. 4 illustrates another two code sequences. In this case, the code sequences are further modulated using a carrier code. In this case, a 10 carrier pair is used to transmit a +1 code bit and a 01 carrier pair is used for a 0 code bit. The corresponding carrier pairs and associated code bit values for each code sequence are shown in FIG. 4. Such carrier code modulation has a number of advantages in the illustrated implementation. First, such modulation simplifies the process of satisfying the above noted code criteria as such criteria can be satisfied by the modulated code sequences rather than the base code sequences. In this regard, since each code bit is half 0 and half 1 and includes one transition, the transmitted code will automatically satisfy all of the above noted criteria except for orthogonality. The preferred code selection process therefore reduces to satisfying orthogonality.

Additionally, the carrier code takes the coded signal further away from DC or low frequency interference. By using higher frequency carriers (e.g., multiple carrier pairs per code bit), the resulting signal can be taken further away from DC or low frequency interference so that 1/f noise and power line noise (e.g., ambient light) have a reduced impact on the desired measurements. These higher frequency carriers produce nulls (noise minima) for several harmonics above the carrier frequency. By appropriate selection of the carrier frequency, these nulls can be used to ease anti-aliasing requirements.

Referring again to FIG. 2, the resulting signals transmitted by the sources 206 travel through the medium 208 in the illustrated embodiment. In this case, the medium may be, for example, a patient's finger, ear lobe or nasal septum. Alternatively, in the case of a reflective oximeter, the signal portions reflected from the medium may be detected to obtain information about the medium.

The signals are received by one or more detectors 210 that provide an electrical detector signal proportional to the received optical signal. Such a signal may be an analog current signal. In the illustrated embodiment, a single detector 210 receives the signals from both sources 206, thereby reducing components and costs as is desirable, particularly when the detector 210 is provided as part of a disposable or short life-span probe. Accordingly, the detector signal is a composite signal including contributions from each of the sources 206. As discussed above, the detector signal may be processed by an amplifier circuit and an analog to digital circuit that are not shown in FIG. 2.

In particular, the amplifier circuit outputs an analog voltage signal which is representative of the optical signals (or code division multiplexed signal) from the sources. This analog voltage signal is received by a fast A/D converter which samples the analog voltage signal to generate a digital voltage signal which can be processed by the digital signal processing unit. The converter 112 takes multiple digital samples per time period corresponding to a code value or value of the carrier wave. That is, the sampling rate of the converter is sufficiently fast to take one or more samples and, more preferably at least about 3 samples and, even more preferably at least about 20 samples per "on" or "off" period of each of the sources 102. Such multiple sampling per cycle allows the oximeter to track the shape of the detector signal, to allow for reduced noise processing of the resulting digital signal, to reduce the required A/D converter word length and to identify phase components of interest within a signal cycle. In one implementation, information regarding the shape of the signal may be used in filtering the demodulating signal as discussed below. The code modulated composite signal may be sampled by the converter, for example, at a frequency of about 41,667 Hz. It will thus be appreciated that the values output by the converter 112 are not integrated or aggregate values corresponding to a source cycle period or dark period, but rather, are substantially instantaneous values reflecting the detector signal at a moment within a cycle. The result, in the illustrated embodiment, is that the detector signal as transmitted to the demodulator 214 is a series of digital values where each digital value corresponds to an intensity of the cumulative signals received by the detector at a given time or short time period.

In addition to this digital detector signal, the demodulator 214 also receives filtered demodulation data from demodulation signal module 212. The demodulation data is used to extract, from the composite code division multiplexed detector signal, information regarding the contribution to that composite detector signal from each of the sources. Generally, the demultiplexing process involves processing the composite detector signal using the first code associated with the first source to obtain received intensity information for the first source and processing the composite detector signal using the second code associated with the second source to obtain received intensity information for the second source. In particular, each such demultiplexing signal is generally composed of a series of concatenated code sequences corresponding to the drive signal for that source. The demultiplexing signal is synchronized to the drive signals (e.g., by reference to a common clock or based on a feed forward signal from the analog to digital converter) so that corresponding bits of the detector signal and demultiplexing signal are co-processed. The detector signal can then be demultiplexed by taking the bitwise product of the detector signal and demultiplexing signal for a sampling period (e.g., a short portion of a patient's pulse cycle) to obtain a demultiplexed binary sequence. This demultiplexed binary sequence can then be integrated to obtain a value indicative of the intensity of the detected signal portion attributable to the corresponding source. Such values form the output 216 that is transmitted to a parameter calculation module that executes any of various well-known algorithms for determining oxygen saturation or related parameter values based on signal attenuation or the detected intensity values.

The illustrated demodulation signal module 212 performs a number of functions in generating the demodulation signals. First, as noted above, the module 212 concatenates each of the codes to obtain the base demultiplexing signal form. This signal form is also filtered by the module 212 to obtain an improved demultiplexing signal. In this regard, the demodulation data may be filtered to compensate for signal distortion. Specifically, the discussion above has assumed idealized waveforms. In reality, due to bandwidth limitations and nonlinearities of the various components, the transmitted code is distorted to an extent by the transmission and receiving systems. If these distorted shapes were processed using idealized demultiplexing data, the effects of distortion could have a substantial impact on the resulting measurements. In the illustrated embodiment, the distorted wave shapes are detected by the analog to digital converter and used to filter the demodulation data so that, to a significant extent, the distortion effects are canceled out during demultiplexing and do not affect the resulting calculations. This maximizes signal strength and minimizes channel to channel cross-talk. It will be appreciated that these advantages result from the use of a fast A/D converter in conjunction with code division multiplexing. That is, the ability to represent each code bit of the detector signal and corresponding demultiplexing signal as a stream of multiple digital value allows for compensation relative to distortion of a waveform corresponding to a code bit.

The module 212 can also perform filtering to dampen or eliminate response at particular frequencies. For example, an expected source of noise is related to power line frequencies and harmonics thereof that modulate ambient light and certain electronic noise. The effects of such noise can be reduced, just as channel to channel cross-talk is minimized, by selecting the demodulation values so that processing the detector signal using the demodulation values tends to pass or amplify the desired components and block or de-emphasize the undesired components. That is, the demodulation signal can be modulated with a signal component that has a degree of orthogonality relative to the signal components representing the targeted noise. In this regard, the demodulating signals can be filtered with notch filters at the power line frequency and harmonics thereof to reduce interference. In addition, the demodulation signals may be high pass filtered to reduce response at noisier lower frequencies and low pass filtered to avoid aliasing problems. More generally, it will be appreciated that the demodulation signal may be filtered, modulated or otherwise processed in a variety of ways to more fully discriminate the signal component of interest from cross-talk, noise, distortion or other interference.

The code sequence is repeated in the demodulation signal. Filtering effects such as noted above are also generally repeating, e.g., on a periodic basis. Accordingly, the demodulation signal is generally composed of a repeating series of values that can be stored (once or periodically based on feedback/feedforward data) and need not be computed on the fly. Preferably, the filtered demodulation sequence is pre-computed and stored. More preferably, only a portion of the overall sequence is stored. That is, after perhaps only a few bits, the sequence is similar to previously transmitted data. For many codes, it has been found that storing and concatenating only 3 to 5 bits results in cross-talk between channels of −140 db, even in severely band limited systems. Thus, storage and processing resource requirements can be minimized. Also, using repeated code sequences per each measurement interval (e.g., $\frac{1}{50}$th second) achieves identical signal patterns from each 50 Hz sample.

The system described above including code division multiplexing, carrier based codes and a fast analog to digital converter, has a number of additional advantages. Using the carrier-based codes permits use of AC coupled transmitters and receivers. Such AC coupled transmitters and receivers may be advantageous in that they can reduce the DC offset of the detector signal. Because such DC components tend to be substantially larger than the AC signal of interest, saturation or reduced dynamic range is a concern. This can be avoided by using AC coupled transmitters and receivers. Even when the transmitter and receiver are of the DC type, the front-end amplifier may be AC coupled or use DC restoration as discussed above to reduce DC offset. Also, saturation and reduced dynamic range can be avoided by using a high resolution analog to digital converter, e.g., a 16 bit or greater converter.

The system described above may also use on/off transmitters or analog transmitters with on/off drivers to reduce costs. The on/off transmitters transmit extra power in the frequencies above the fundamental. If anti-aliasing filters are used, the efficiency of the system is lower. When anti-aliasing filters are not used, the system must have substantially greater bandwidth than is required for proper reception of the code. However, the losses due to on/off transmission are offset by the simplicity of the drive.

Figure 5:
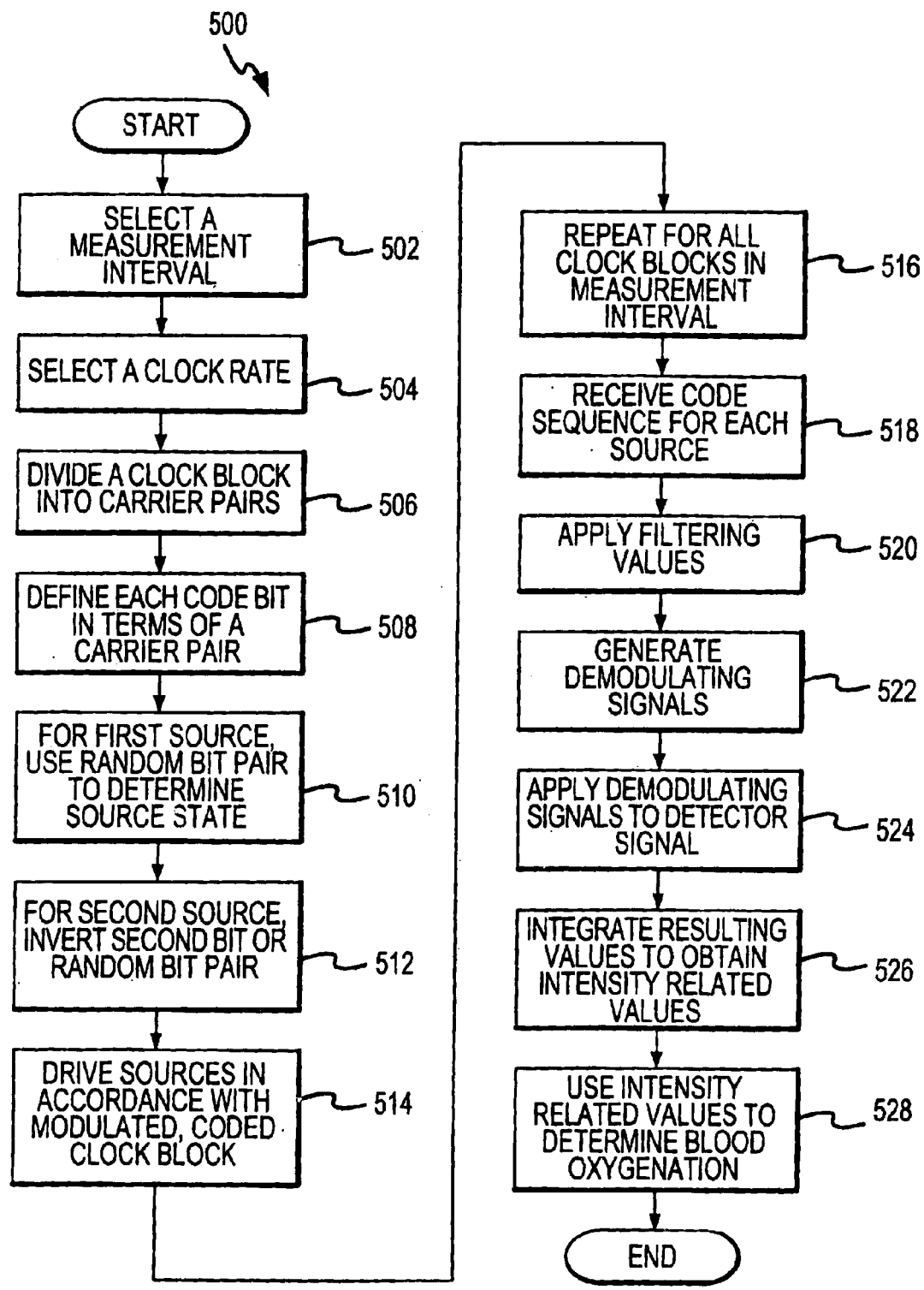
FIG. 5 is a flowchart illustrating a code division multiplexing process in accordance with the present invention.

The code division multiplexing process of the present invention can be summarized by reference to the flowchart of FIG. 5. The illustrated process 500 sets forth a specific example in the context of a two source pulse oximetry system where the codes are determined based on the output of a random number generator. It will be appreciated that various aspects of the methodology are more broadly applicable to alternative pulse oximetry implementations and other signal attenuation measurement environments.

The process 500 is initiated by selecting (502) a measurement interval. this will be the minimum time interval for which light intensity measurements can be obtained. Once the measurement interval is obtained, a clock rate is selected (504) for light source switching. This will be the minimum time for which any source can be turned on or off. The measurement interval and clock rate are preferably chosen so that, for a system with M light sources, each measurement interval has an integer number of clock blocks where each block has $2^M$ clocks. In the case of two sources, the measurement interval preferably has an integer number of clock blocks each having 4 clocks.

The process continues by dividing (506) each clock block into carrier pairs. Thus, in the case of the illustrated embodiment, a clock block is divided into two carriers pairs where each carrier pair defines a code bit. That is, each clock block includes four clocks or two code bits. An integer number of such clock blocks is included within each measurement interval. In addition, each code bit is defined (508) in terms of a carrier pair. Thus, for example, a code bit "1" may be defined as a carrier pair "10." A code bit of "0" may be defined as a carrier pair of "01."

The output of a random bit generator may be used (510) to determine the state of the first source. Thus, for example, if the random bit generator outputs a bit pair of "00," this may be modulated as a "0101" for purposes of driving the first source. For the second source, the second bit of this random bit pair is inverted (512). That is, the second source drive is encoded as "01." It will be appreciated that this bit pair is orthogonal to the bit pair used to drive the first source. The 01 code of the second source is modulated as "0110" in terms of the carrier pairs.

The sources are then driven (514) in accordance with the modulated, coded clock blocks. Specifically, in the case of the above-noted example, the first source is driven to transmit 0101 during the first clock block while the second source is driven to transmit 0110. This process is then repeated (516) for all clock blocks in a measurement interval.

On the receiver side, the demultiplexing module receives (518) the corresponding code sequence for each source. The module then applies (520) filtering values to these code sequences and generates (522) demodulating signals. These demodulating signals are applied (524) to the detector signal to produce a stream of values corresponding to the contributions of each of the sources. These values are then integrated (526) to obtain intensity related values which can then be used (528) to determine blood oxygen saturation or related parameter values.

Figure 6:
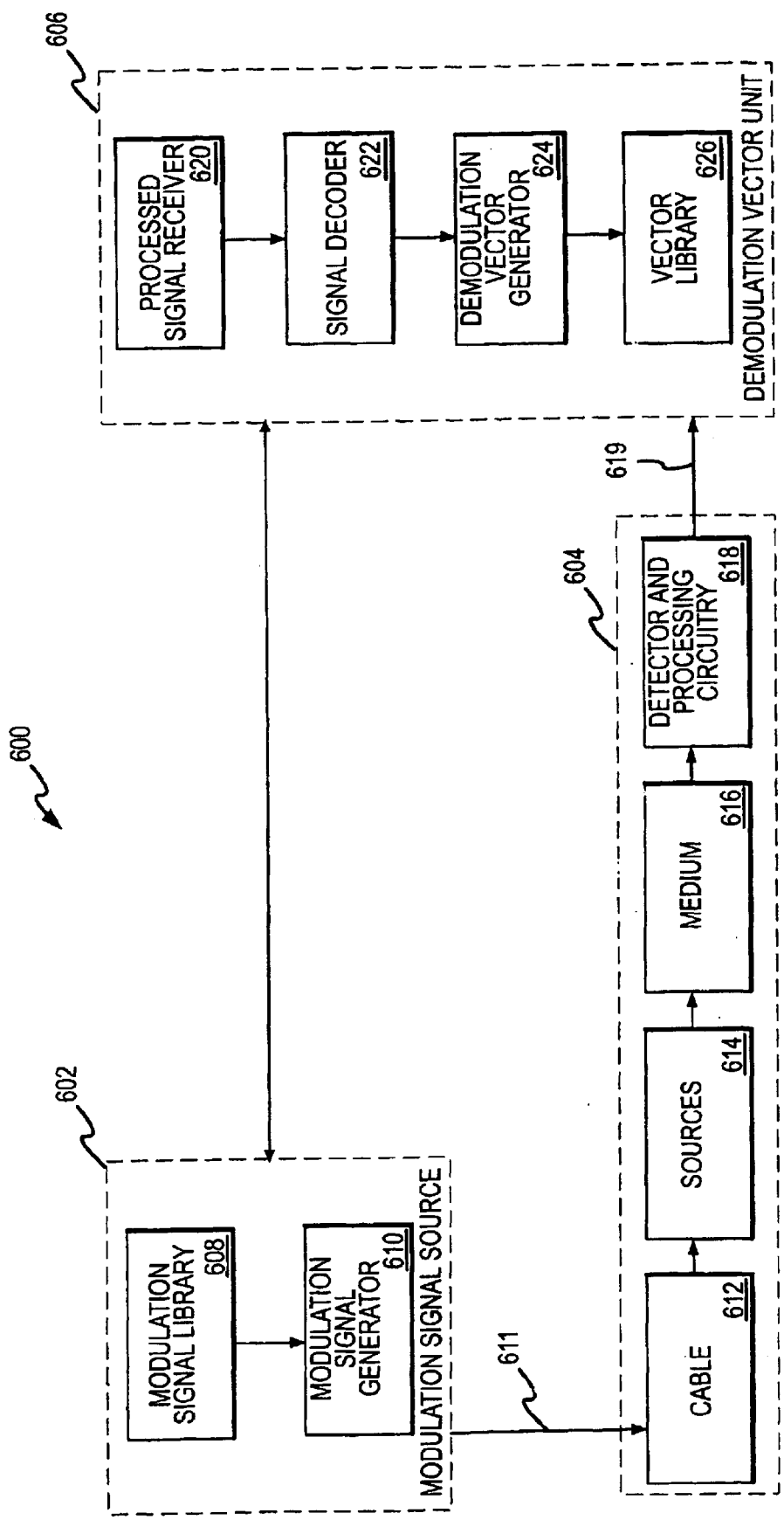
FIG. 6 is a schematic diagram of demodulation code generator for use in manufacturing or calibration.
Figure 7:
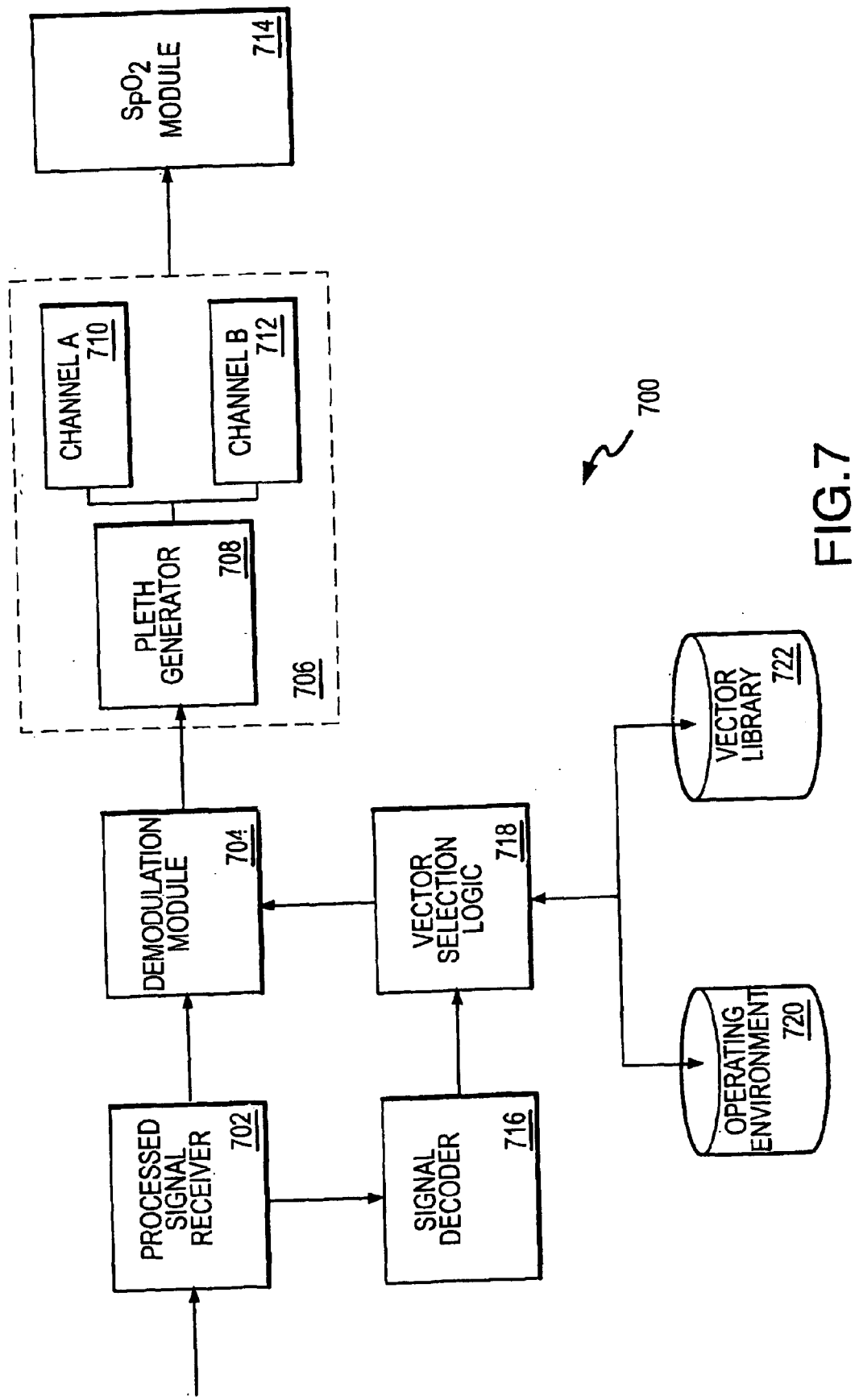
FIG. 7 is a schematic diagram of a pulse oximeter processing unit implementing vector selection and lock-out logic in accordance with the present invention.
Figure 8:
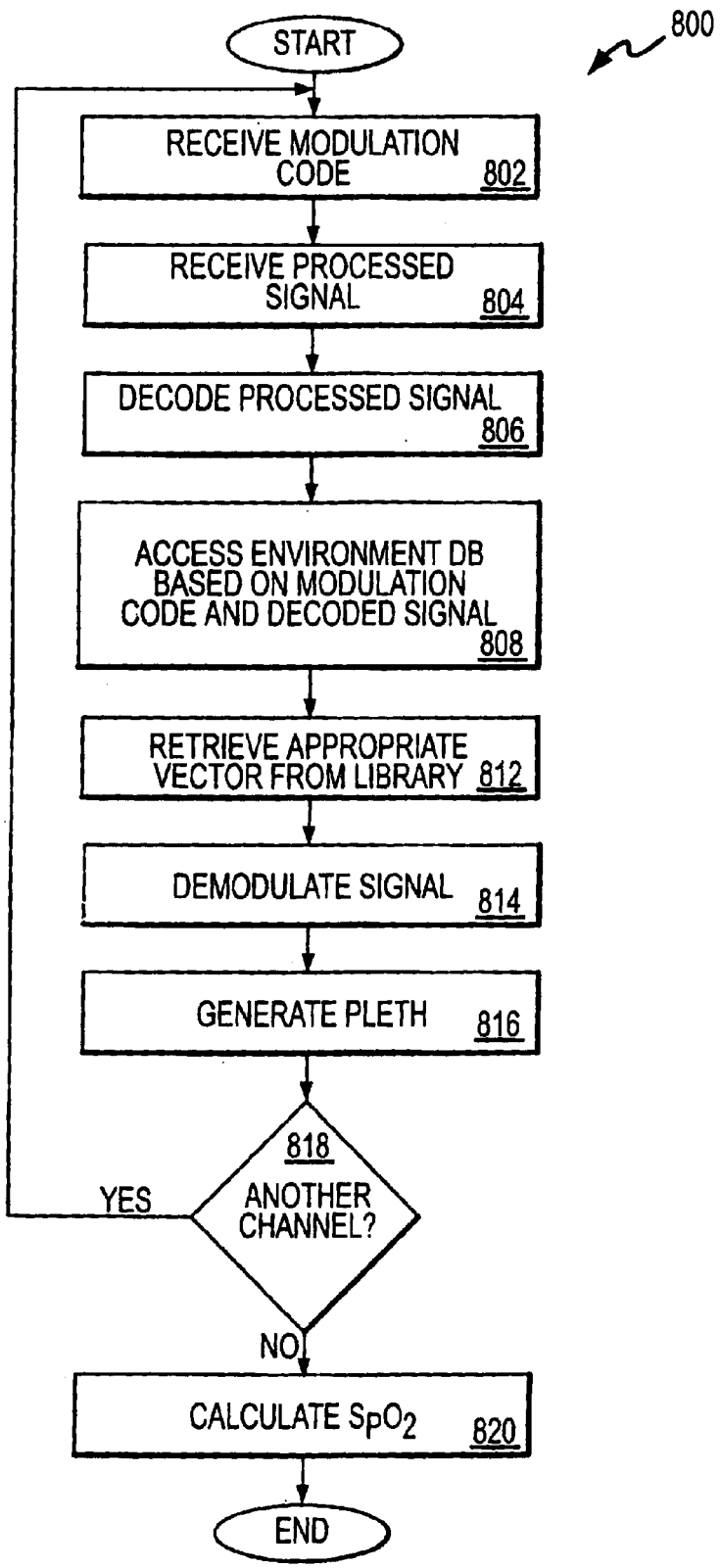
FIG. 8 is a flow chart illustrating a run-time process for vector selection and lock-out in accordance with the present invention.

As noted above, it has been found that distortion of the modulation codes due to particular operating environments can result in increased cross-talk or impaired noise rejection if not compensated for. In particular, it has been found advantageous to establish orthogonality of the demodulation vectors relative to the signal as received at the processor rather than the modulated signal as originally generated. This process can be optimized relative to particular operating environments, i.e., particular equipment configurations, transmission media, etc. FIGS. 6–8 illustrate a particular implementation in this regard. Specifically, the following figures illustrate a process for first performing tests to characterize a particular operating environment and generate appropriate demodulating vectors and then to use the optimized demodulation vectors during run-time (i.e., during operation of a pulse oximeter in a patient monitoring setting) to identify an operating environment, select appropriate vectors or, alternatively, to lock-out an unauthorized or otherwise unsupported equipment configuration.

Referring to FIG. 6, a system 600 for generating modulation vectors based on particular operating environments is illustrated. The system 600 includes a modulation signal source 602, a variable operating environment 604 and a demodulation vector unit 606. The modulation signal source 602 includes a modulation signal generator 610 for outputting a modulation signal 611 based on a modulation signal library 608. The modulation signal 611 preferably has characteristics as described above, including orthogonality, fairly even distribution of 1s and 0s, etc. Such codes may be stored in the library 608. Alternatively, code segments may be stored in the signal library 608 and then concatenated to form full code strings by the signal generator 610.

A primary purpose of the system 600 is to characterize different operating environments and generate corresponding demodulation vectors. Accordingly, the operating environment 604 may be varied to test different operating environment components. In the context of pulse oximetry, important variables relate to the optical sources, the optical detector, and associated circuitry as well as the appendage involved. For example, it may be desirable to test and optimize an instrument in connection with various combinations of probes and cables that may be used in the field. The illustrated operating environment is shown as including a cable 612, sources 614, medium 616 and detector and processing circuitry 618. As a practical matter, the sources 614 and detector and processing circuitry 618 may be included within a particular probe unit. Similarly, the cable 612 may be any of various commercially available cables. It is believed that adequate results for many applications can be obtained by testing a particular instrument model with various combinations of probe types and cable types. That is, for many applications, a particular probe type and cable type combination can be tested once to generate appropriate demodulation vectors for the instrument under consideration. However, it may be advantageous to test each individual instrument and each individual cable and probe rather than characterizing the instrument, cable and probe based on type. Moreover, it may prove beneficial to update the demodulation vectors for any given combination of instrument cable and probe periodically or on a case-by-case basis. Accordingly, the system 600 may be incorporated into a pulse oximetry unit. The medium 616 may be a signal attenuator designed to model a patient appendage or, in the case of run-time calibration, may be the actual patient appendage.

The results of interaction of the modulation signal 611 with the operating environment 604 is a processed modulation signal 619, which is different than the modulation signal 611. The differences are due, for example, to distortion resulting from processing of the signal by the operating environment 604. This processed modulation signal 619 is provided to a demodulation vector unit 606 for generating appropriate demodulation vectors. The illustrated unit 606 includes a processed signal receiver 620, a signal decoder 622, a demodulation vector generator 624 and a vector library 626.

The functionality of the processed signal receiver 620 may vary depending on the particular application. In this regard, some probes may include substantial signal amplification and conditioning components. Other probes may provide a relatively raw detector signal, i.e., an analog current signal representative of the received optical signal. In the illustrated embodiment, the unit 606 receives an analog current signal. Accordingly, the processed signal receiver 620 includes amplification circuitry and an analog to digital converter as described above. In particular, the receiver 620 preferably incorporates a fast A/D converter that provides multiple digital sample values corresponding to a particular bit of the modulation code. Such a fast A/D converter allows for substantial resolution in developing demodulation vectors that are optimized for particular operating environments.

The output of the processed signal receiver 620 is a digital signal. This digital signal is optionally analyzed by the signal decoder 622 to generate a signal representing the processed signal 619. This signal may be filtered to have a standardized bit rate, though this bit rate may be different than the bit rate of the modulation signal 611. The resulting decoded signal is then provided to a demodulation vector generator 624 that generates an optimized demodulation vector based on the decoded signal. In this regard, the demodulation vector generator 624 may implement algorithms to generate demodulation vectors having preferred characteristics as described above. The demodulation vectors generated by generator 624 are then stored in a vector library 626. It will be appreciated that the library 626 may store demodulation vectors for each supported operating environment permutation for a given instrument as well as for the different channels of that instrument. The resulting library can then be transferred into the memory of the pulse oximetry instrument in the case of a manufacturing application or simply stored in memory in the case where the demodulation vector unit 606 is incorporated into the instrument.

FIG. 7 illustrates a processor of a pulse oximeter implementing vector selection logic and lock-out logic in accordance with the present invention. The processor 700 generally includes a processed signal receiver 702, a demodulation module 704, a pleth module 706 and an oxygenation calculation (SpO$_2$) module 714. The processed signal receiver 702 receives an output signal from an A/D converter, preferably a fast A/D converter as described above. For example, the receiver 702 may be an appropriate port of a digital signal processor. The received signal is provided to a demodulation module 704 which may be implemented in software running on the digital signal processor. The demodulation module demodulates the received signal based on application of selected demodulation vectors, as well be described below, and thereby provides an output that can be analyzed to provide information regarding the individual channels of the detector signal. The output of the demodulation module is processed by a pleth generator 708 to generate information representative of pleth waveforms corresponding to the channels of the pulse oximeter, in this case labeled channel (710) and (712). For example, these channels may correspond to the red and infrared sources typically included in pulse oximeters. Finally, these pleth waveforms can be used by the SpO2 module 714 to provide an output regarding blood oxygenation by executing known algorithms.

In order to allow for vector selection based on recognition of a particular operating environment, the received signal may be processed by a signal decoder 716. As discussed above, demodulation vectors may be generated relative to standardized input signals. The signal decoder 716 is therefore operative to express the received signal in terms of a standardized bit stream that may be recognized by the vector selection logic 718. The vector selection logic 718 then compares the decoded signal to signal information stored in the operating environment database 720 to identify any match. If the decoded signal matches that of an approved operating environment for code division multiplexing, then the vector selection logic can access an appropriate demodulation vector from the vector library 722. The resulting demodulation vector is then provided to the demodulation module 704 for demodulating the received signal.

FIG. 8 is a flowchart illustrating an associated run-time or calibration process 800. The process 800 is initiated by receiving (802) a modulation code. For example, the modulation code may be obtained from the modulation signal generator or may simply be stored in memory for a particular unit. The process 800 further involves receiving (804) a processed signal and decoding (806) the processed signal to obtain a standardized decoded signal. This decoded signal may then be used to access (808) an operating environment database. In particular, the decoded signal may be used to retrieve (812) an appropriate demodulation vector from the vector library. This vector can then be used to demodulate (814) the received signal and generate (816) an appropriate pleth for oxygenation calculations as described above. This process may be repeated for other channels (818) (if all channels are not processed simultaneously) of the pulse oximeter until all channels have been demodulated. At that point, blood oxygenation can be calculated (820).

Figure 9:
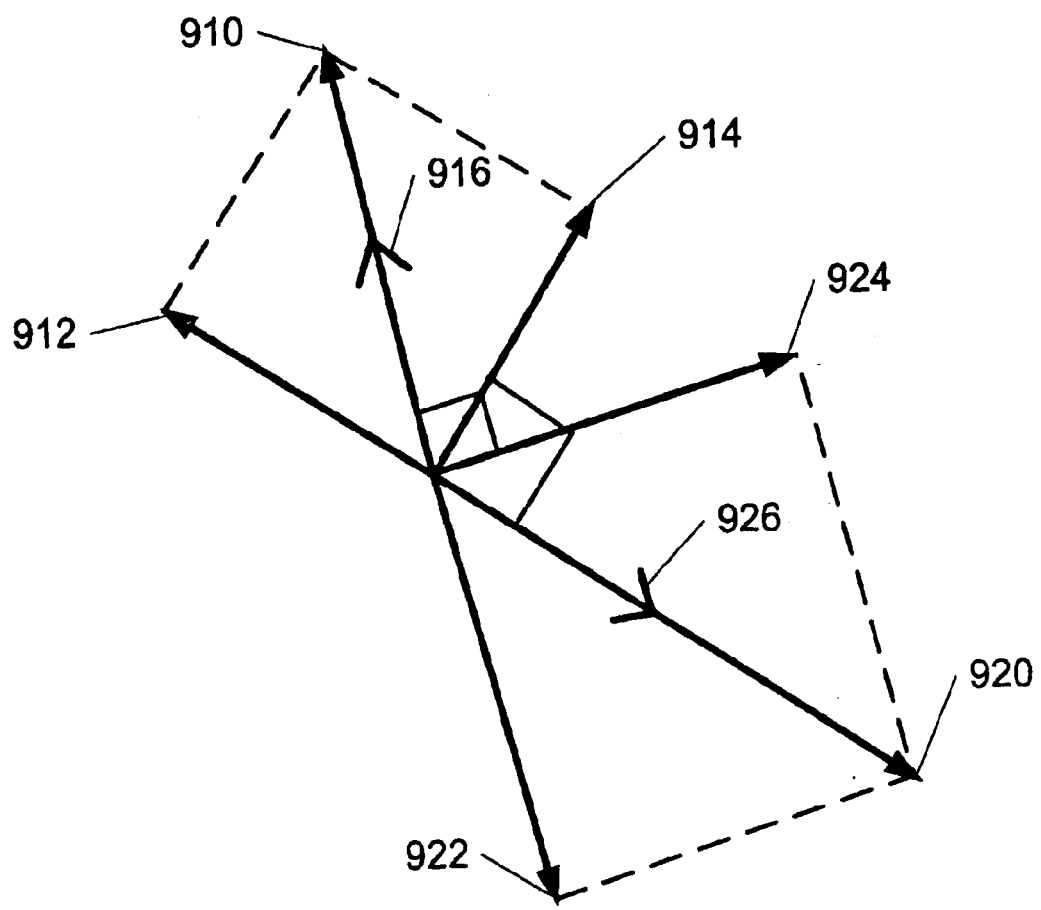
FIG. 9 is a vector diagram illustrating one manner of obtaining optimized demodulation vectors in accordance with the present invention.

Referring now to FIG. 9, the previously discussed code division multiplexed pulse oximeter excites the light signal sources using codes that are preferably mathematically orthogonal to one another. However, even though the excitation codes may be designed to produce orthogonal output (e.g., no IR output due to Red illumination and vice versa) the orthogonality of the composite signal output by the detector may be degraded as a result of offsets, feed throughs and other cross talks. This situation is illustrated by the vector diagram of FIG. 9. In this regard, the Red data vector 910 represents the signal output by the detector when only the Red LED is excited and the IR data vector 920 represents the signal output by the detector when only the IR LED is excited. As indicated by the obtuse angle between them, the Red and IR data vectors 910, 920 are non-orthogonal.

One manner of generating demodulation vectors for obtaining the output signal on each channel is to excite only one of the sources (e.g., the Red LED) and measure the detector output sequence. The measured detector output sequence is then used as the demodulation vector for subsequent demodulation of the composite signal to obtain the data for that particular channel (e.g., the Red channel). However, demodulating the composite signal using demodulation vectors generated in this manner does not remove the undesired cross talk present in the non-orthogonal signal components of the detector signal. For example, demodulation of the detector output signal using a demodulation vector generated by exciting the IR LED by itself results in cross talk of the Red channel onto the IR channel represented by the Red to IR cross talk vector 912. Likewise, demodulation of the detector output signal using a demodulation vector generated by exciting the Red LED by itself results in cross talk of the IR channel onto the Red channel represented by IR to Red cross talk vector 922.

Demodulation vectors that are orthogonal to the data on the other channels present in the composite signal can be obtained by subtracting the cross talk vectors from their respective data vectors. For example, a Red demodulation vector 914 is obtained by subtracting the Red to IR cross talk vector 912 from the Red data vector 910, and an IR demodulation vector 924 is obtained by subtracting the IR to Red cross talk vector 922 from the IR data vector 920. As is shown, the Red and IR demodulation vectors 914, 924 are not orthogonal to each other, but rather the Red demodulation vector 914 is orthogonal to the IR data vector 920 so that no IR data is demodulated into the Red channel and the IR demodulation vector 924 is orthogonal to the Red data vector 910 so that no Red data is demodulated into the IR channel. In this regard, undesired cross talk between the channels of the pulse oximeter is substantially reduced or eliminated.

Figure 10:
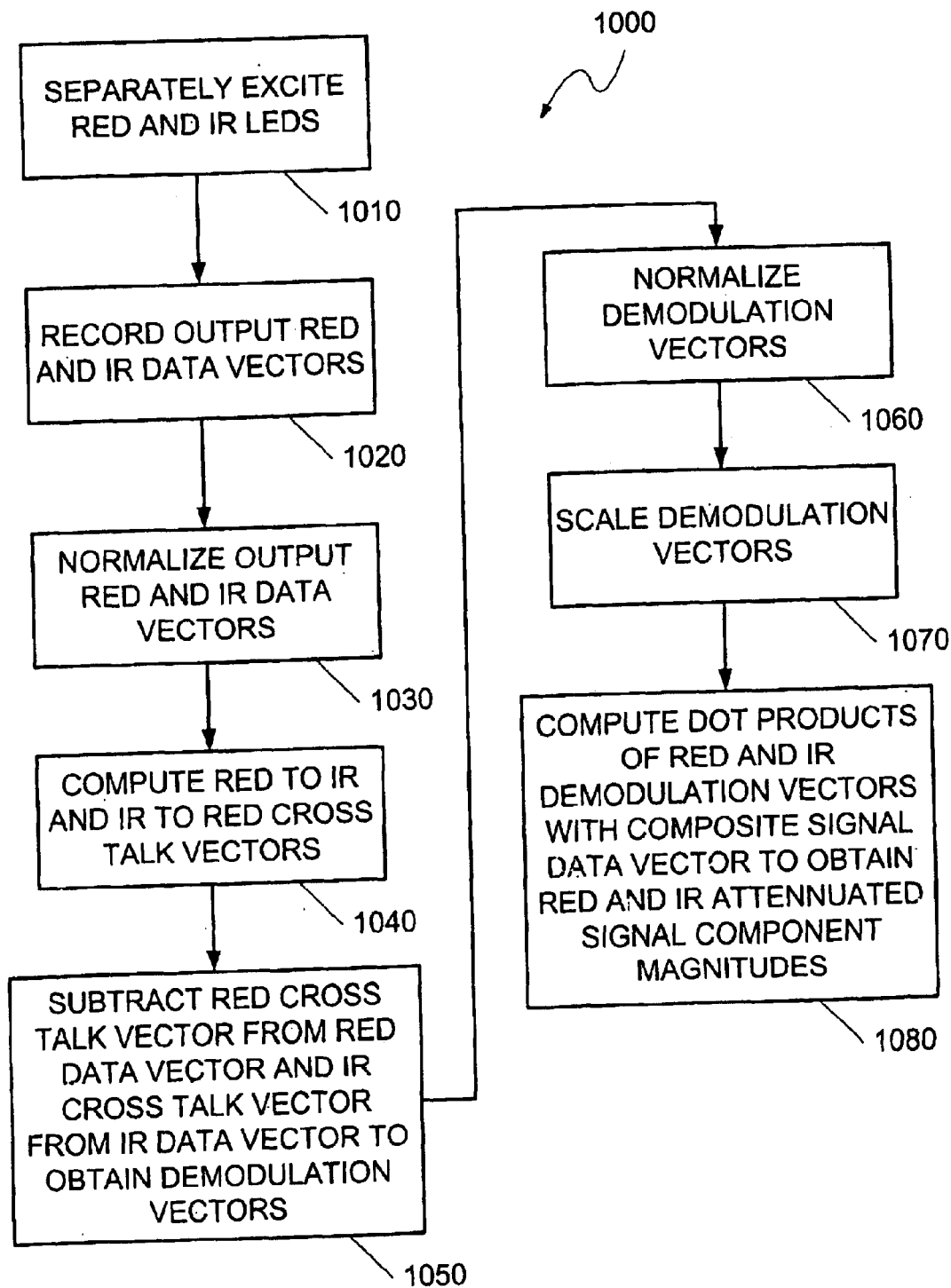
FIG. 10 is a flow chart summarizing the steps involved in generating the optimized demodulation vectors shown graphically in FIG. 9.

Referring now to FIG. 10 there is shown a flowchart summarizing the steps involved in generating the Red and IR demodulation vectors 914, 924 shown graphically in FIG. 9 and using the demodulation vectors 914, 924 to obtain the magnitudes of respective Red and IR signal components present in a composite signal data vector obtained by a pulse oximeter.

The process (1000) involves separately exciting (1010) the Red and IR LEDs and measuring (1020) the respective Red and IR data vectors 910, 920 output by the detector. A system 600 such as shown in FIG. 6 may be used for this purpose. The Red and IR LEDs are preferably excited for multiple cycles of the drive code sequence with the each data point of the Red and IR data vectors 910, 920 being averaged over the number of cycles to increase the signal-to-noise ratio of the Red and IR data vectors 910, 920. The Red and JR data vectors 910, 920 are then normalized (1030) to unit length Red and IR data vectors 916, 926. This may be accomplished by dividing each vector 910, 920 by its respective length. The Red to IR and IR to Red cross talk vectors 912, 922 are then computed (1040). In this regard, the Red to JR cross talk vector 912 may be computed as a vector having a length equal to the dot product of the normalized Red and IR data vectors 916, 926 with its direction being opposite that of the normalized IR data vector 926. The IR to Red cross talk vector 922 may be computed as a vector having a length equal to the dot product of the normalized Red and IR data vectors 916, 926 with its direction being opposite that of the normalized Red data vector 916. The desired Red and JR demodulation vectors 914, 924 are then obtained by subtracting (1050) the respective cross talk vectors 912, 922 from the respective normalized data vectors 916, 926. In this regard, the Red to IR cross talk vector 912 is subtracted from the normalized Red data vector 916 and the IR to Red cross talk vector 922 is subtracted from the normalized IR data vector 926.

Once obtained, the demodulation vectors 914, 916 may be used to obtain the magnitude of the Red and IR signal components in the composite signal output by an operating pulse oximeter. In this regard, the demodulation vectors 914, 916 may be normalized (1060) by dividing the vectors by their respective lengths to obtain normalized demodulation vectors. The normalized demodulation vectors may then be arbitrarily scaled (1070) to satisfy the desire of generally having integer calculations in the demodulation process which avoids floating point operations, rounding errors and the like. The magnitudes of the Red and IR signal components are obtained by computing (1080) the dot product of the composite signal data vector with the normalized (and scaled) Red demodulation and IR demodulation vectors, respectively.

Although process (1000) of generating demodulation vectors has been described in connection with a two channel (Red and IR) pulse oximeter, it should be noted that the process (1000) may be utilized to generate demodulation vectors in pulse oximeters and other devices that utilize attenuated optical signals to derive information therefrom having two, three, four or more channels, regardless of the wavelengths of the light signals utilized for each channel.

As previously mentioned, the composite signal from the detector may include signal patterns due for example, to cross talk between channels and/or capacitive cross talk between the emitter for a particular channel and the detector. Such signal patterns are typically non-orthogonal to the demodulation waveforms used to obtain the desired demodulated signals. The demodulation waveforms (also referred to herein as demodulation or demultiplexing vectors) that are multiplied with the composite signal output by the detector to demodulate the individual channels essentially comprise matched filters since the demodulation waveforms look like the signals to be demodulated. Matched filters can be generated for each channel and each interference using, for example, a system 600 such as shown in FIG. 6. In this regard, a matched filter for each channel and interference may be obtained by recording each signal and interference alone multiple times using the system 600. Static bias (e.g., DC offset) is subtracted from each recording to avoid including constant terms and each recording for a particular signal or interference is averaged to remove random noise from each matched filter. Once the shape of each signal and interference is recorded, the similarity of each interfering signal to each desired signal can be computed by calculating the cross correlation at time =0, or taking the summation of the instant by instant product of the two waveforms. This computed similarity represents the amount of one signal that demodulates in the other signal.

Figure 11:
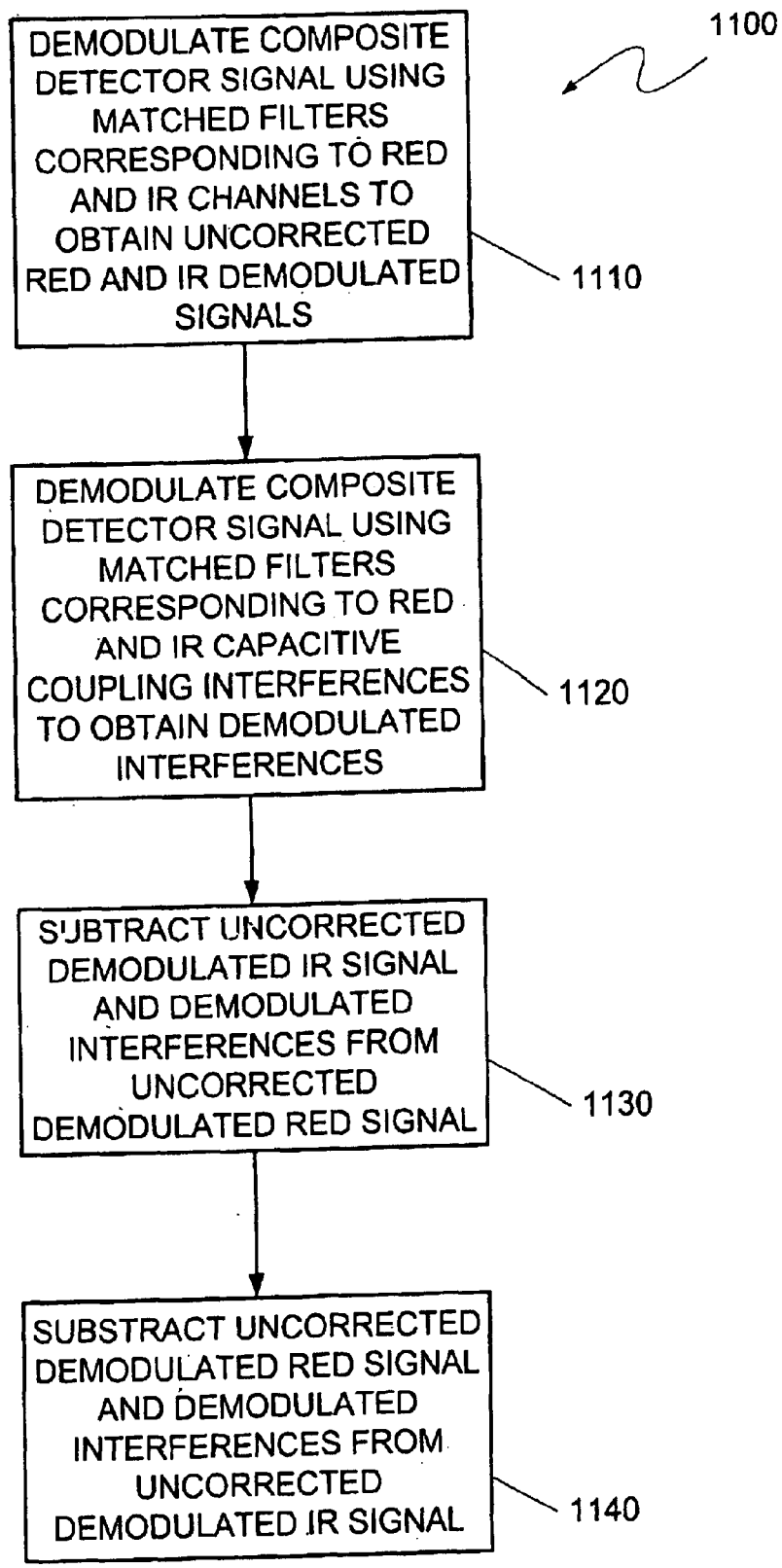
FIG. 11 is a flow chart showing one embodiment of a process of correcting for non-orthogonal patterns in the composite detector signal in accordance with the present invention.

Having obtained the necessary matched filters, one manner of correcting for non-orthogonal patterns in the composite detector signal is summarized by the flowchart shown in FIG. 11. The process (1100) begins with demodulating (1110) the composite detector signal using the matched filters for each channel to obtain uncorrected demodulated signals corresponding to each channel. The composite detector signal is also demodulated (1120) using the matched filters for each interference to obtain demodulated signals corresponding to each interference (e.g., cross-talk resulting from capacitive coupling). The corrected demodulated signal for a particular channel is then obtained by subtracting (1130) the uncorrected demodulated signal(s) corresponding to the other channel(s) and subtracting (1140) the demodulated interference(s) from the uncorrected demodulated signal for the desired channel obtained in step (1110). For example, to obtain the corrected demodulated Red signal in a two channel Red and IR pulse oximeter, the composite detector signal is demodulated (1110) using the Red demodulation waveform to obtain an uncorrected demodulated Red signal. The composite detector signal is also demodulated (1110, 1120) using the IR demodulation waveform to obtain the uncorrected demodulated IR signal as well as demodulation waveforms for Red capacitive coupling and IR capacitive coupling to obtain the demodulated Red capacitive and IR capacitive interferences. The uncorrected demodulated IR signal and the demodulated Red capacitive and IR capacitive interferences are then subtracted (1130, 1140) from the uncorrected demodulated Red signal to generate the corrected demodulated Red signal. To obtain the corrected demodulated IR signal, the uncorrected demodulated Red signal and the demodulated Red capacitive and IR capacitive interferences are then subtracted (1130, 1140) from the uncorrected demodulated IR signal to generate the corrected demodulated IR signal.

The previously described process (1100) shown in FIG. 11 of correcting for non-orthogonal patterns in the composite detector signal works best where the Red and IR waveform shapes generally remain constant over the time period of interest, but does not require that the magnitudes of the interfering signal(s) remain constant. In this regard, the cross talk between the Red and IR channels may be computed from the following expressions for the uncorrected Red and IR signals:

$$ru = \sum_n Rd \cdot (r \cdot Rd + i \cdot Id) = r \cdot \sum_n Rd^2 + i \cdot \sum_n Rd \cdot Id \text{ and}$$

$$iu = \sum_n Id \cdot (r \cdot Rd + i \cdot Id) = r \cdot \sum_n Rd \cdot Id + i \cdot \sum_n Id^2$$

where (r*Rd+i*Id) is the composite detector signal output from the detector;

Rd and Id are the Red and IR demodulation tables;

ru and iu are the uncorrected Red and IR demodulated values;

r and i are the corrected Red and IR demodulated values; and n is the number of samples over which to correct for cross talk.

Substituting the following:

$$R = \sum_n Rd^2 \quad I = \sum_n Id^2 \quad X = \sum_n Rd \cdot Id$$

in the above two expressions for the uncorrected Red and IR demodulated values results in the following system of two equations with two unknowns, r and i:

$$ru = r \cdot R + i \cdot X$$

$$iu = r \cdot X + i \cdot I$$

The above system of equations may be solved to obtain the following expressions for r and i:

$$r = \frac{(iu \cdot X - I \cdot ru)}{(X^2 - I \cdot R)} \text{ and } i = \frac{(ru \cdot X - R \cdot iu)}{(X^2 - I \cdot R)}$$

The above expressions for the corrected Red and IR values, r and i, do not account for scaling due to the manner in which the uncorrected Red and IR values, ru and iu, are defined. In this regard, as X goes to zero, scaled corrected Red and IR values are given by:

$$rs = r \cdot R \text{ and } is = i \cdot I$$

Substituting for r and i and grouping constants, the following expressions for the scaled corrected Red and IR values, rs and is, are obtained:

$$rs = ru \cdot \left(R \cdot \frac{I}{I \cdot R - X^2}\right) - iu \cdot \left(R \cdot \frac{X}{I \cdot R - X^2}\right) \text{ and}$$

$$is = iu \cdot \left(I \cdot \frac{R}{I \cdot R - X^2}\right) - ru \cdot \left(I \cdot \frac{X}{I \cdot R - X^2}\right)$$

While the previously described approach to correcting for non-orthogonal patterns in the composite detector signal does not require modification of the demodulation waveforms for each channel, it does require demodulation of the composite detector signal for each channel and each interference for which correction is desired. As may be appreciated, this is can be a computational and memory intensive approach to correcting for non-orthogonal patterns in the composite detector signal.

Figure 12:
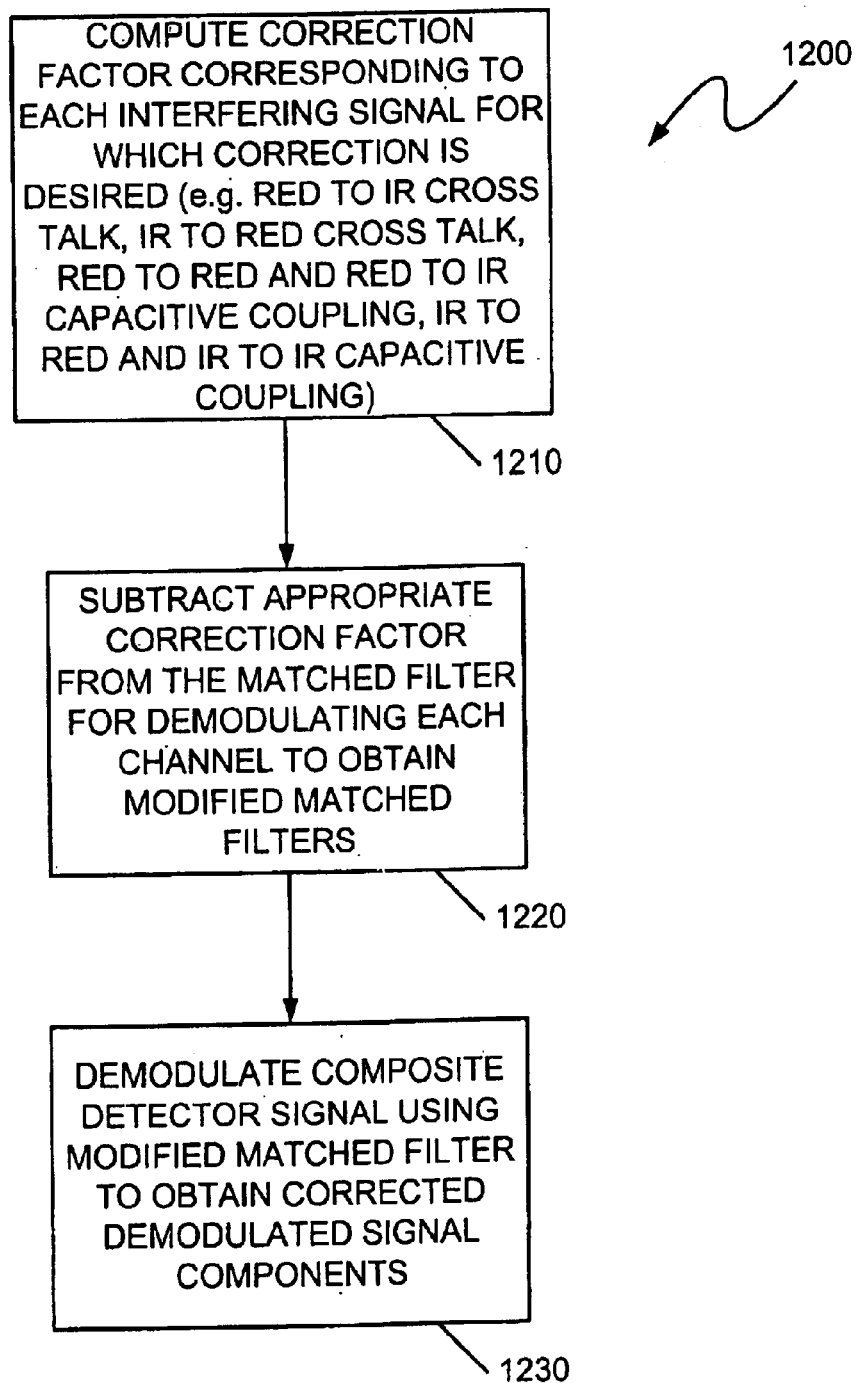
FIG. 12 is a flow chart showing another embodiment of a process of correcting for non-orthogonal patterns in the composite detector signal in accordance with the present invention.

An alternative approach to correcting for non-orthogonal patterns in the composite detector signal is shown in the flowchart of FIG. 12. The process (1200) involves computing (1210) a correction factor corresponding to each interfering signal for which correction is desired. The matched filter for a particular channel is then modified (1220) by subtracting the appropriate correction factors from the matched filter for such channel to obtain a modified matched filter. The composite detector signal is then demodulated (1230) using the modified matched filter for a particular channel to obtain the corrected demodulated signal on that channel.

Each of the steps (1210, 1220, and 1230) is performed for each sample instant. In this regard, correction coefficients may be computed simultaneously for each channel. For example, a correction coefficient for correcting for cross talk from the IR channel into Red channel may be determined from the following expression for the demodulated Red signal:

$$rd = \sum_{k=1}^{n} (R_k + cir \cdot I_k)(r \cdot R_k + i \cdot I_k)$$

where cir is the IR to Red cross talk correction coefficient;

rd is the demodulated Red signal;

r and i are the amplitudes of the Red and IR signals;

$R_k$ and $I_k$ are the Red and IR waveform shapes at each instant k;

n is the duration for application of correction;

$(r^*R_k+i^*I_k)$ is the incoming signal to be demodulated at each instant k; and $(R_k+cir^*I_k)$ is the modified Red demodulation waveform at each instant k.

The above expression for the demodulated Red signal may be solved to obtain the following expression for the IR to Red correction coefficient:

$$cir = \frac{-\sum_{k=1}^{n} R_k \cdot I_k}{\sum_{k=1}^{n} (I_k)^2}$$

Thus, the IR to Red correction coefficient, cir, depends only on the instantaneous values of the Red and IR waveform shapes, $R_k$ and $I_k$.

In a similar fashion, the correction coefficient for correcting for cross talk from the Red channel into IR channel may be determined from the following expression for the demodulated IR signal:

$$id = \sum_{k=1}^{n} (I_k + cri \cdot R_k)(r \cdot R_k + i \cdot I_k)$$

where cri is the Red to IR cross talk correction coefficient;

id is the demodulated IR signal;

r and i are the amplitudes of the Red and IR signals;

$R_k$ and $I_k$ are the Red and IR waveform shapes at each instant k;

n is the duration for application of correction;

$(r^*R_k+i^*I_k)$ is the incoming signal to be demodulated at each instant k; and $(I_k+cri^*R_k)$ is the modified IR demodulation waveform at each instant k.

The above expression for the demodulated IR signal may be solved to obtain the following expression for the Red to IR correction coefficient:

$$cri = \frac{-\sum_{k=1}^{n} R_k \cdot I_k}{\sum_{k=1}^{n} (R_k)^2}$$

Thus, the Red to IR correction coefficient, cri, also depends only on the instantaneous values of the Red and IR waveform shapes, $R_k$ and $I_k$.

The previously described computations for the IR to Red and Red to IR correction coefficients, cri and cri, did not account for possible capacitive cross talk. In this regard, correction coefficients for correcting for cross talk from the IR channel into the Red channel, Red capacitive coupling into the Red channel, and IR capacitive coupling into the Red channel may be determined from the following expression for the demodulated Red signal:

$$rd = \sum_{k=1}^{n} (R_k + cir \cdot I_k + ccrr \cdot Cr_k + ccir \cdot Ci_k)(r \cdot R_k + i \cdot I_k + cr \cdot Cr_k + ci \cdot Ci_k)$$

where cir is the IR to Red cross talk correction coefficient;

ccrr is the Red capacitive coupling into Red correction coefficient;

ccir is the IR capacitive coupling into Red correction coefficient;

rd is the demodulated Red signal;

r and i are the amplitudes of the Red and IR signals;

cr and ci are the capacitive cross talk from the Red and IR channels;

$R_k$ and $I_k$ are the Red and IR waveform shapes at each instant k;

$Cr_k$ and $Ci_k$ are the capacitive Red and IR waveform shapes at each instant k;

n is the duration for application of correction;

$(r*R_k+i*I_k+cr*Cr_k+Ci*Ci_k)$ is the incoming signal to be demodulated at each instant k; and $(R_k+cir*I_k+ccrr*Cr_k+ccir*Ci_k)$ is the modified Red demodulation waveform at each instant k for all ks in the measurement interval.

The above expression for the demodulated Red signal may be expanded, like terms collected, and, recognizing that in order to make the demodulated Red signal independent of i, the ci, and cr, each group of terms set equal to zero to obtain a system of three equations with the three correction coefficients, cir, ccrr, and ccir as unknowns. The system of equations may be solved to obtain the following solution, expressed in matrix form, for the three correction coefficients, cir, ccrr, and ccir:

$$\begin{pmatrix} cir \\ ccrr \\ ccir \end{pmatrix} = \begin{pmatrix} II & CrI & CiI \\ ICr & CrCr & CiCr \\ ICi & CrCi & CiCi \end{pmatrix}^{-1} \cdot - \begin{pmatrix} IR \\ CrR \\ CiR \end{pmatrix}$$

where $IR = \sum_{k=1}^{n} R_k I_k$, $CrR = \sum_{k=1}^{n} R_k Cr_k$, $CiR = \sum_{k=1}^{n} R_k Ci_k$, -continued $II = \sum_{k=1}^{n} I_k I_k$, $ICr = \sum_{k=1}^{n} I_k Cr_k$, $ICi = \sum_{k=1}^{n} I_k Ci_k$, $CrI = \sum_{k=1}^{n} Cr_k I_k$, $CrCr = \sum_{k=1}^{n} Cr_k Cr_k$, $CrCi = \sum_{k=1}^{n} Cr_k Ci_k$, $CiI = \sum_{k=1}^{n} Ci_k I_k$, $CiCr = \sum_{k=1}^{n} Ci_k Cr_k$, and $CiCi = \sum_{k=1}^{n} Ci_k Ci_k$.

In a similar manner, correction coefficients for correcting for cross talk from the Red channel into the IR channel, IR capacitive coupling into the IR channel, and Red capacitive coupling into the IR channel may be determined from the following expression for the demodulated IR signal:

$$id = \sum_{k=1}^{n} (I_k + cri \cdot R_k + ccii \cdot Ci_k + ccri \cdot Cr_k)(r \cdot R_k + i \cdot I_k + cr \cdot Cr_k + ci \cdot Ci_k)$$

where cri is the Red to IR cross talk correction coefficient;

ccii is the IR capacitive coupling into IR correction coefficient;

ccri is the Red capacitive coupling into IR correction coefficient;

id is the demodulated IR signal;

r and i are the amplitudes of the Red and IR signals;

cr and ci are the capacitive cross talk from the Red and IR channels;

$R_k$ and $I_k$ are the Red and IR waveform shapes at each instant k;

$Cr_k$ and $Ci_k$ are the capacitive Red and IR waveform shapes at each instant k;

n is the duration for application of correction;

$(r*R_k+i*Ik+cr*Cr_k+ci*Ci_k)$ is the incoming signal to be demodulated at each instant k; and $(I_k+cri*R_k+ccii*Ci_k+ccri*Cri_k)$ is the modified IR demodulation waveform at each instant k for all ks in the measurement interval.

The above expression for the demodulated IR signal may be expanded, like terms collected, and, recognizing that in order to make the demodulated IR signal independent of i, the ci, and cr, each group of terms set equal to zero to obtain a system of three equations with the three correction coefficients, cri, ccii, and ccri as unknowns. The system of equations may be solved to obtain the following solution, expressed in matrix form, for the three correction coefficients, cri, ccii, and ccri:

$$\begin{pmatrix} cri \\ ccii \\ ccri \end{pmatrix} = \begin{pmatrix} RR & CiR & CrR \\ RCr & CiCr & CrCr \\ RCi & CiCi & CrCi \end{pmatrix}^{-1} \cdot - \begin{pmatrix} RI \\ CiI \\ CrI \end{pmatrix}$$

where $RI = \sum_{k=1}^{n} R_k I_k$, $CiI = \sum_{k=1}^{n} I_k Ci_k$, $CrI = \sum_{k=1}^{n} I_k Cr_k$, $RR = \sum_{k=1}^{n} R_k R_k$, $RCr = \sum_{k=1}^{n} R_k Cr_k$, $RCi = \sum_{k=1}^{n} R_k Ci_k$, $CiR = \sum_{k=1}^{n} Ci_k R_k$, -continued $$CiCr = \sum_{k=1}^{n} Ci_k Cr_k, \; CiCi = \sum_{k=1}^{n} Ci_k Ci_k, \; CiR = \sum_{k=1}^{n} Cr_k R_k,$$

$$CrCr = \sum_{k=1}^{n} Cr_k Cr_k, \text{ and } CrCi = \sum_{k=1}^{n} Cr_k Ci_k.$$

The modified demodulation waveforms work well under a variety of conditions. Since the correction coefficients are computed at each sample instant, the modified demodulation waveforms adjust to capacitive cross talk and interfering light signal levels that vary over time. However, in order to correct for varying cross talk wave form shapes due, for example, to changing system bandwidths and photodetector tailing, modification of the initial demodulation waveforms to which the correction coefficients are applied may be necessary. In this regard, initial demodulation waveforms may be obtained using, for example, system 600 that are close to orthogonal for all interfering signals for which correction is desired. In this regard, a plurality of interfering waveform shapes covering the entire span of waveform shapes can be obtained. Data from multiple probes at differing drive and light signal levels (including opaque for capacitive data) may be obtained. Where waveform shapes covering the entire span of interfering waveform shapes cannot be obtained, simulated waveform shapes may be generated. A regression technique such as, for example, the linear least squares algorithm is then applied to create a demodulation waveform that is a similar as possible to the matched filter waveform and as orthogonal as possible to all other waveforms. Alternatively, a singular value decomposition technique may be applied to the obtained data to extract pertinent features of an orthogonal demodulation vector.

While various embodiments of the present invention have been described in detail, further modifications and adaptations of the invention may occur to those skilled in the art. However, it is to be expressly understood that such modifications and adaptations are within the spirit and scope of the present invention.

What is claimed is:

1. A method for demodulating at least first and second attenuated signal components within a composite signal output by at least one detector of a pulse oximeter, the first and second attenuated signal components corresponding to first and second multiplexed signals that are emitted by first and second optical signal sources of the pulse oximeter, attenuated by a patient tissue site and received by the detector, said method comprising the steps of:

generating a first demodulation vector for demodulating the first attenuated signal component from the composite signal, the first demodulation vector being orthogonal to the second attenuated signal component of the composite signal;

generating a second demodulation vector for demodulating the second attenuated signal component from the composite signal, the second demodulation vector being substantially orthogonal to the first attenuated signal component of the composite signal;

demodulating the composite signal with the first demodulation vector to obtain a magnitude of the first attenuated signal component; and demodulating the composite signal with the second demodulation vector to obtain a magnitude of the second attenuated signal component.

2. The method of claim 1 wherein said steps of generating a first demodulation vector and generating a second demodulation vector are performed prior to using the pulse oximeter and wherein the first and second demodulation vectors remain fixed while the pulse oximeter is used to monitor a patient.

3. The method of claim 1 wherein said steps of generating a first demodulation vector and generating a second demodulation vector are performed prior to using the pulse oximeter to monitor a patient and wherein said method further comprises the step of:

adjusting the first and second demodulation vectors dynamically while the pulse oximeter is used.

4. The method of claim 3 wherein said step of adjusting the first and second demodulation vectors comprises applying at least one correction factor dynamically computed from information included in at least the first and second attenuated signal components of the composite signal.

5. The method of claim 4 wherein said first and second multiplexed signals comprise Red and IR signals and said first and second signal components are Red and IR signal components, and wherein said at least one correction factor is selected from a group consisting of a Red signal to IR signal component cross talk correction factor, an IR signal to Red signal component cross talk correction factor, a Red optical signal source capacitive coupling to Red signal component correction factor, a Red optical signal source capacitive coupling to IR signal component correction factor, an IR optical signal source capacitive coupling to IR signal component correction factor, and an IR optical signal source capacitive coupling to Red signal component correction factor.

6. The method of claim 1 wherein the composite signal comprises a digital signal, wherein the first and second demodulation vectors comprise digital signals, and wherein said steps of demodulating the composite signal with the first demodulation vector and demodulating the composite signal with the second demodulation vector are performed in a digital processor.

7. The method of claim 1 wherein said steps of generating a first and a second demodulation vector comprise the steps of:

operating only the first optical signal source of the pulse oximeter;

recording a first data vector output from the detector when only the first optical signal source is operated;

operating only the second optical signal source of the pulse oximeter;

recording a second data vector output from the detector when only the second optical signal source is operated;

computing a first scalar value corresponding to cross talk from operation of the second optical signal source into the first data vector;

computing a second scalar value corresponding to cross talk from operation of the first optical signal source into the second data vector;

forming a first correction vector having a direction opposite the direction of the first data vector and a magnitude given by the first scalar value;

forming a second correction vector having a direction opposite the direction of the second data vector and a magnitude given by the second scalar value;

subtracting the first correction vector from the first data vector to obtain the first demodulation vector; and subtracting the second correction vector from the second data vector to obtain the second demodulation vector.

8. The method of claim 7 wherein said step of computing a first scalar value comprises computing a dot product of the first data vector and the second data vector, and wherein said step of computing a second scalar value comprises computing a dot product of the second data vector and the first data vector.

9. The method of claim 1 wherein the first and second multiplexed signals are code division multiplexed signals.

10. The method of claim 1 wherein said steps of generating a first and a second demodulation vector comprises the steps of:
obtaining data output by the detector for a plurality of pulse oximetry probes operated under different drive signal and transmitted light signal levels; and
applying a regression technique to the obtained data to derive the first and second demodulation waveforms.

11. The method of claim 1 wherein said steps of generating a first and a second demodulation vector comprises the steps of:
obtaining data output by the detector for a plurality of pulse oximetry probes operated under different drive signal and transmitted light signal levels; and
applying a singular value decomposition technique to the obtained data to derive the first and second demodulation waveforms.

12. A method of correcting for undesired non-orthogonal signal components and interferences in a composite pulse oximetry signal output by at least one detector of a pulse oximeter, said method comprising the steps of:
demodulating the composite pulse oximetry signal using a first matched filter corresponding to a first signal component present in the composite pulse oximetry signal that is associated with a first wavelength light signal attenuated by a patient tissue site and a second matched filter corresponding to a second signal component present in the composite pulse oximetry signal that is associated with a second wavelength light signal attenuated by a patient tissue site to obtain at least first and second uncorrected demodulated signal components corresponding to the first and second signal components;
demodulating the composite pulse oximetry signal using a third matched filter corresponding to a first interference present in the composite pulse oximetry signal and a fourth matched filter corresponding to a second interference present in the composite pulse oximetry signal to obtain at least first and second demodulated interferences; and
subtracting the second uncorrected demodulated signal component and the first and second demodulated interferences from the first uncorrected demodulated signal component to obtain a first corrected demodulated signal component corresponding to the first signal component.

13. The method of claim 12 wherein the second signal component is associated with an R wavelength light signal attenuated by a patient tissue site, the first interference comprises capacitive coupling from a first wavelength optical signal source into the first signal component and the second interference comprises capacitive coupling from a second wavelength optical signal source into the first signal component.

14. The method of claim 12 further comprising:
demodulating the composite pulse oximetry signal using a fifth matched filter corresponding to a third interference present in the composite pulse oximetry signal and a sixth matched filter corresponding to a fourth interference present in the composite pulse oximetry signal to obtain at least third and fourth demodulated interferences; and
subtracting the first uncorrected demodulated signal component and the third and fourth demodulated interferences from the second uncorrected demodulated signal component to obtain a second corrected demodulated signal component corresponding to the second signal component.

15. The method of claim 14 wherein in the first interference comprises capacitive coupling from a first wavelength optical signal source into the first signal component, the second interference comprises capacitive coupling from a second wavelength optical signal source into the first signal component, the third interference comprises capacitive coupling from the first wavelength optical signal source into the second signal component, and the fourth interference comprises capacitive coupling from the second wavelength optical signal source into the second signal component.

16. The method of claim 12 wherein the composite pulse oximetry signal comprises a digitized signal having a plurality of sample instances and wherein said demodulating and subtracting steps are performed by a digital processor for each sample instance of the digitized composite pulse oximetry signal.

17. The method of claim 12 wherein the first wavelength light signal comprises a Red wavelength light signal and wherein the second wavelength light signal comprises an IR wavelength light signal.

18. A reduced cross talk pulse oximetry system comprising:
at least first and second optical signal sources operable to transmit first and second multiplexed signals;
at least one detector operable to detect the first and second multiplexed signals after the first and second multiplexed signals are attenuated by a patient tissue site and output an analog composite signal including at least first and second attenuated signal components corresponding to the attenuated first and second multiplexed signals;
an analog-to-digital converter operable to convert the analog composite signal to a digital composite signal having a plurality of sample instances; and
a digital processor operable to demodulate the digital composite signal with a first demodulation vector to obtain a magnitude of the first attenuated signal component and demodulate the digital composite signal with a second demodulation vector to obtain a magnitude of the second attenuated signal component, wherein said first demodulation vector is orthogonal to the second attenuated signal component and the second demodulation vector is orthogonal to the first attenuated signal component.

19. The system of claim 18 further comprising:
a demodulation vector unit operable to provide the first and second demodulation vectors to the digital processor.

20. The system of claim 19, wherein the demodulation vector unit is operable to select the first and second demodulation vectors based on an identification of an operating environment.

21. The system of claim 20 wherein the demodulation vector unit is enabled to receive manually entered information from a user of the pulse oximetry system, said manually entered information identifying the operating environment.

22. The system of claim 20 wherein the demodulation vector unit is enabled to automatically identify the operating environment by operating at least one of said first and second optical signal sources to transmit a signal modulated in accordance with a known code and comparing an attenuated signal received by said detector with a library of processed modulated signals.

23. The system of claim 19 wherein said digital processor is further operable to dynamically adjust the first and second demodulation vectors provided by the demodulation vector unit during operation of the pulse oximetry system.

24. The system of claim 23 wherein said digital processor is operable to dynamically adjust the first and second demodulation vectors by subtracting at least one correction factor from said first and second demodulation vectors.

25. The system of claim 24 wherein said digital processor is operable to compute said at least one correction factor for each sample instance of said digital composite signal.

26. The system of claim 24 wherein said first and second optical signal sources comprise Red and IR wavelength optical signal sources, said first and second signals comprise Red and IR signals and said first and second signal components comprise Red and IR signal components, and wherein said at least one correction factor is selected from a group consisting of a Red signal to IR signal component cross talk correction factor, an IR signal to Red signal component cross talk correction factor, a Red optical signal source capacitive coupling to Red signal component correction factor, a Red optical signal source capacitive coupling to IR signal component correction factor, an IR optical signal source capacitive coupling to IR signal component correction factor, and an IR optical signal source capacitive coupling to Red signal component correction factor.

27. The system of claim 18 said first and second optical signal sources are operable to transmit first and second code division multiplexed signals.

* * * * *

UNITED STATES PATENT AND TRADEMARK OFFICE
CERTIFICATE OF CORRECTION

PATENT NO.    : 6,778,923 B2
DATED         : August 17, 2004
INVENTOR(S)   : Norris et al.

It is certified that error appears in the above-identified patent and that said Letters Patent is hereby corrected as shown below:

Column 29,
Lines 56-58, delete "the second signal component is associated with an R wavelength light signal attenuated by a patient tissue site,".

Column 30,
Line 11, delete the word "in".

Signed and Sealed this

Nineteenth Day of July, 2005

JON W. DUDAS
*Director of the United States Patent and Trademark Office*